(12) United States Patent
Zivkovic et al.

(10) Patent No.: US 8,721,599 B2
(45) Date of Patent: *May 13, 2014

(54) DUAL CHAMBER PASSIVE RETRACTION NEEDLE SYRINGE

(75) Inventors: Ivan Zivkovic, Pleasantville, NY (US); Russell Cole, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/187,045

(22) Filed: Jul. 20, 2011

(65) Prior Publication Data

US 2012/0022464 A1   Jan. 26, 2012

Related U.S. Application Data

(60) Provisional application No. 61/366,749, filed on Jul. 22, 2010.

(51) Int. Cl.
*A61M 5/00* (2006.01)
*A61M 5/32* (2006.01)
*A61M 5/178* (2006.01)

(52) U.S. Cl.
USPC ............ 604/187; 604/192; 604/183; 604/181

(58) Field of Classification Search
USPC ......... 604/110, 192, 197–198, 506, 183, 195, 604/187, 218, 181
See application file for complete search history.

(56) References Cited

U.S. PATENT DOCUMENTS

| | | | |
|---|---|---|---|
| 3,055,362 A * | 9/1962 | Uytenbogaar | ................ 604/144 |
| 4,375,815 A | 3/1983 | Burns | |
| 4,388,925 A | 6/1983 | Burns | |
| 4,449,529 A | 5/1984 | Burns | |
| 4,527,561 A | 7/1985 | Burns | |
| 4,535,769 A | 8/1985 | Burns | |
| 4,553,541 A | 11/1985 | Burns | |
| 4,616,649 A | 10/1986 | Burns | |
| 4,624,253 A | 11/1986 | Burns | |
| 4,677,979 A | 7/1987 | Burns | |
| 4,941,883 A * | 7/1990 | Venturini | ....................... 604/186 |
| 5,431,672 A | 7/1995 | Cote et al. | |
| 5,451,210 A * | 9/1995 | Kramer et al. | ................. 604/137 |
| 5,531,694 A * | 7/1996 | Clemens et al. | ............... 604/110 |
| 5,533,970 A | 7/1996 | Berger et al. | |
| 5,578,011 A | 11/1996 | Shaw | |
| 5,632,733 A | 5/1997 | Shaw | |
| 5,752,968 A | 5/1998 | Jolly et al. | |
| 5,792,162 A | 8/1998 | Jolly et al. | |
| 5,797,880 A | 8/1998 | Erskine | |
| 5,830,190 A | 11/1998 | Howell | |

(Continued)

FOREIGN PATENT DOCUMENTS

| | | |
|---|---|---|
| WO | WO-96/35463 | 11/1996 |
| WO | WO-98/48869 | 11/1998 |
| WO | WO-03/090815 | 11/2003 |

*Primary Examiner* — Bhisma Mehta
*Assistant Examiner* — Bradley G Thomas, Jr.
(74) *Attorney, Agent, or Firm* — Servilla Whitney LLC

(57) ABSTRACT

Embodiments of a retractable syringe assembly are provided that include a dual syringe barrel configuration. In one or more embodiments, the assemblies include a fluid barrel for retaining fluid and a retraction barrel for housing the retraction feature and the needle hub assembly. The assemblies include a trigger element that moves with the plunger rod to activate the retraction feature within the retraction mechanism.

32 Claims, 27 Drawing Sheets

(56) References Cited

U.S. PATENT DOCUMENTS

| | | |
|---|---|---|
| 5,919,201 A | 7/1999 | Carter et al. |
| 5,938,676 A | 8/1999 | Cohn et al. |
| 5,941,892 A | 8/1999 | Cohn et al. |
| 6,010,486 A | 1/2000 | Carter et al. |
| 6,036,674 A | 3/2000 | Caizza et al. |
| 6,053,929 A | 4/2000 | Cohn et al. |
| 6,086,568 A | 7/2000 | Caizza |
| 6,090,077 A | 7/2000 | Shaw |
| 6,177,037 B1 | 1/2001 | Mayer |
| 6,183,440 B1 | 2/2001 | Bell |
| 6,221,052 B1 | 4/2001 | Caizza et al. |
| 6,368,303 B1 | 4/2002 | Caizza |
| 6,409,701 B1 | 6/2002 | Cohn |
| 6,413,237 B1 | 7/2002 | Caizza et al. |
| 6,432,087 B1 | 8/2002 | Hoeck et al. |
| 6,517,516 B1 | 2/2003 | Caizza |
| 6,558,357 B1 | 5/2003 | Hoeck |
| 6,585,690 B1 | 7/2003 | Hoeck et al. |
| 6,599,268 B1 | 7/2003 | Townsend et al. |
| 6,632,198 B2 | 10/2003 | Caizza |
| 6,689,106 B2 | 2/2004 | Bush, Jr. et al. |
| 6,776,776 B2 | 8/2004 | Alchas et al. |
| 6,840,291 B2 | 1/2005 | Caizza |
| 6,926,700 B2 | 8/2005 | Bressler et al. |
| 6,932,803 B2 | 8/2005 | Newby |
| 6,952,604 B2 | 10/2005 | DeNuzzio et al. |
| 7,018,344 B2 | 3/2006 | Bressler et al. |
| 7,083,599 B2 | 8/2006 | Alchas et al. |
| 7,108,675 B2 | 9/2006 | Deboer et al. |
| 7,182,734 B2 | 2/2007 | Saulenas et al. |
| 7,258,678 B2 | 8/2007 | Wilkinson et al. |
| 7,294,118 B2 | 11/2007 | Saulenas et al. |
| 7,344,517 B2 | 3/2008 | Schiller |
| 7,351,224 B1 | 4/2008 | Shaw |
| 7,426,408 B2 | 9/2008 | DeNuzzio et al. |
| 7,597,684 B2 | 10/2009 | Alchas et al. |
| 7,604,613 B2 | 10/2009 | Crawford et al. |
| 7,713,245 B2 | 5/2010 | Cipoletti et al. |
| 2003/0125676 A1 | 7/2003 | Swenson et al. |
| 2003/0125677 A1 | 7/2003 | Swenson et al. |
| 2003/0163096 A1 | 8/2003 | Swenson et al. |
| 2003/0181867 A1 | 9/2003 | Bressler et al. |
| 2005/0215951 A1 | 9/2005 | Saulenas et al. |
| 2006/0129173 A1 | 6/2006 | Wilkinson |
| 2007/0129675 A1 | 6/2007 | Summerville et al. |
| 2007/0260193 A1 | 11/2007 | Chin et al. |
| 2008/0097344 A1 | 4/2008 | McKinnon et al. |
| 2008/0243075 A1 | 10/2008 | Shaw |
| 2009/0048560 A1* | 2/2009 | Caizza et al. ............... 604/110 |
| 2009/0131869 A1 | 5/2009 | Caizza et al. |

* cited by examiner

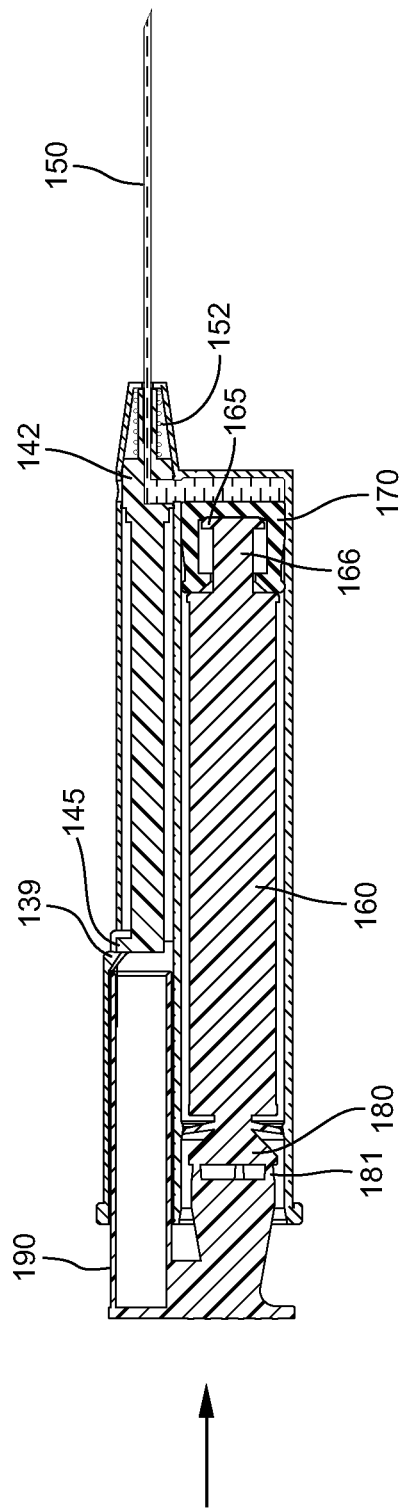
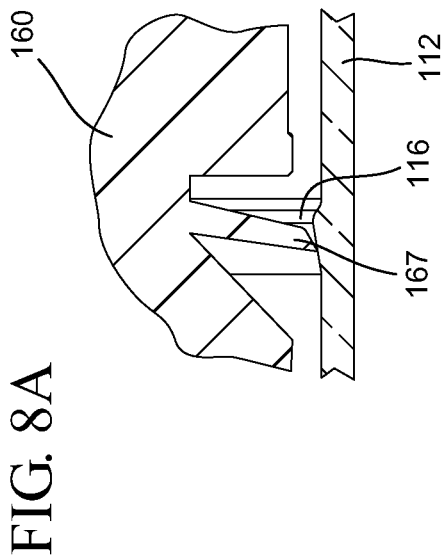
FIG. 8
FIG. 8A

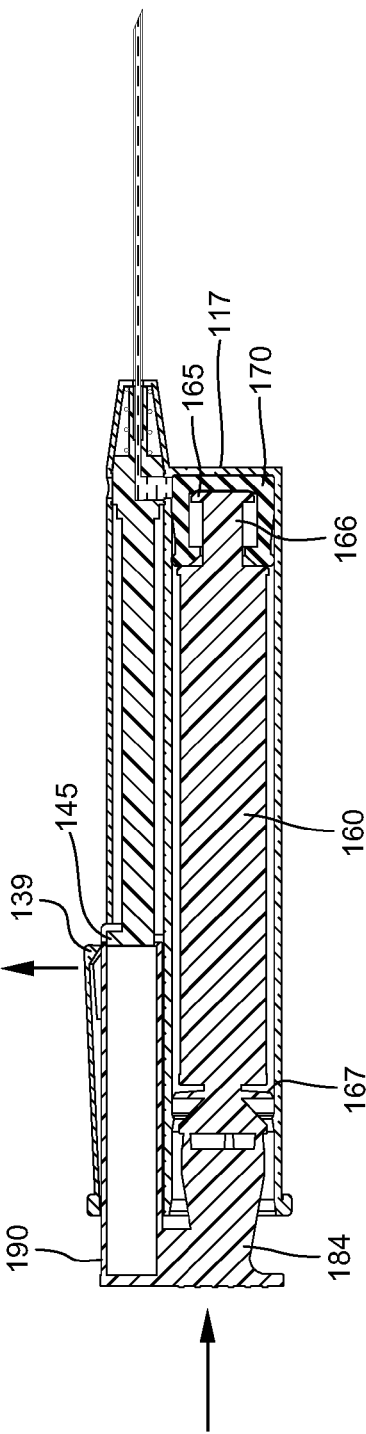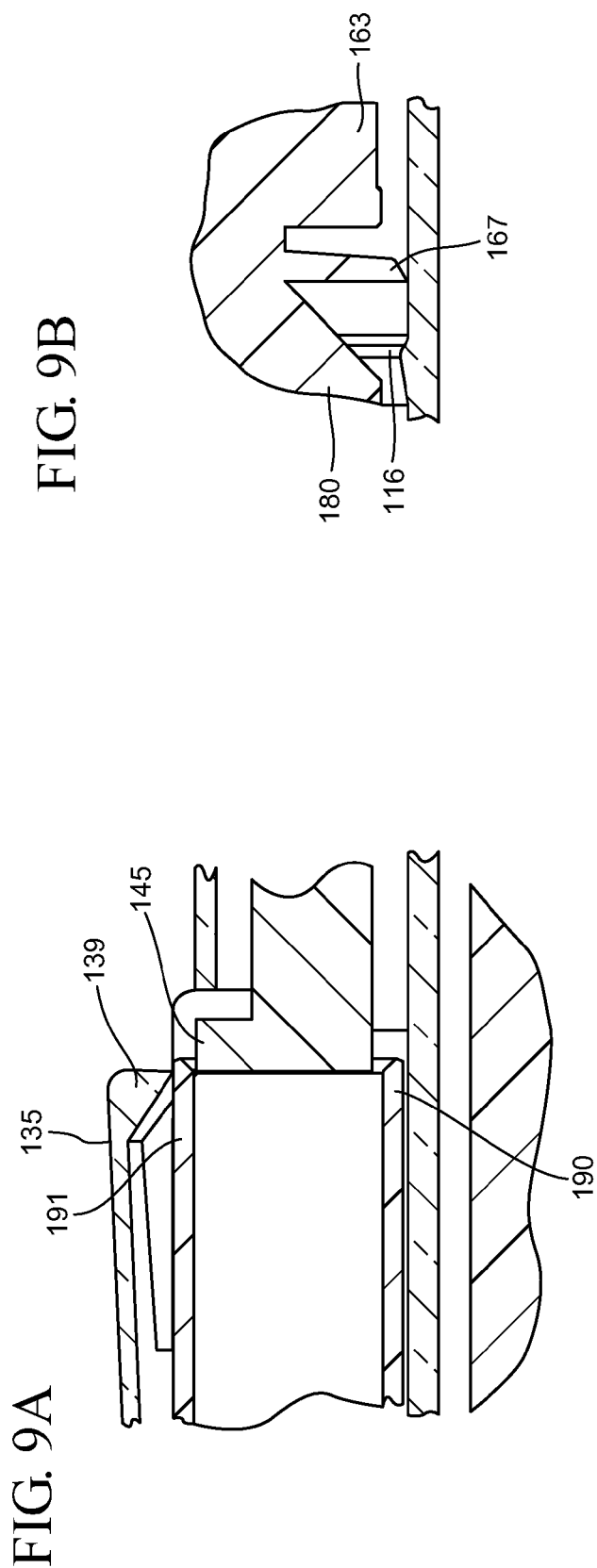
FIG. 9
FIG. 9A
FIG. 9B

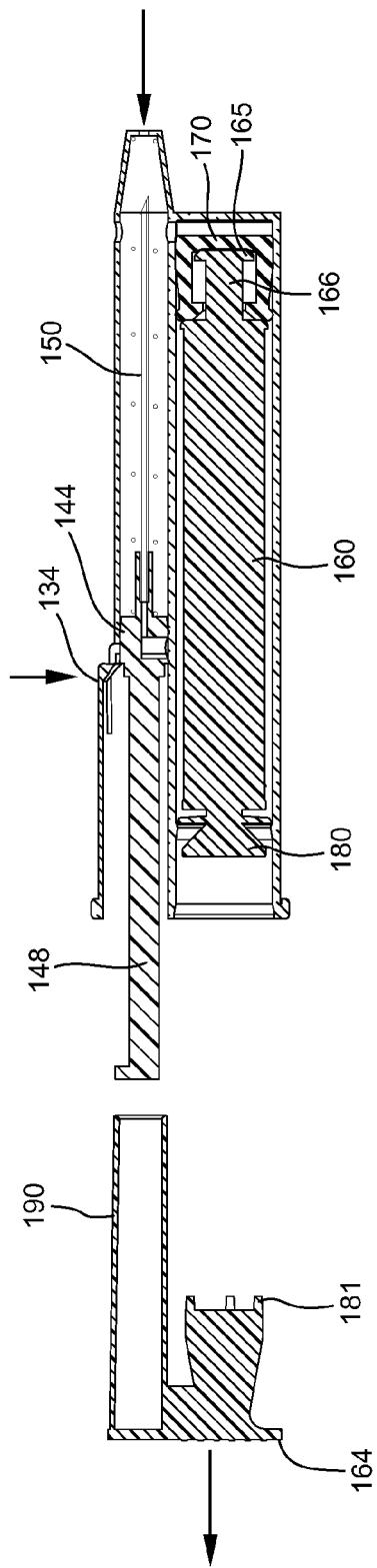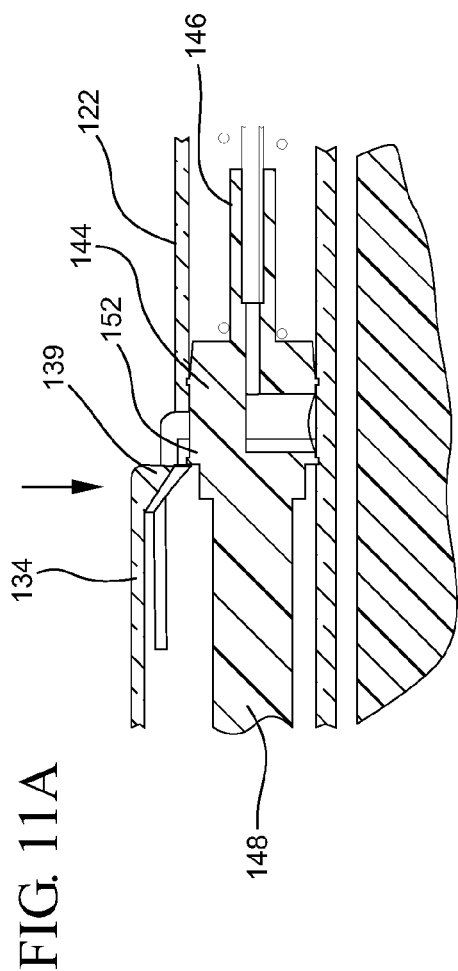
FIG. 11
FIG. 11A

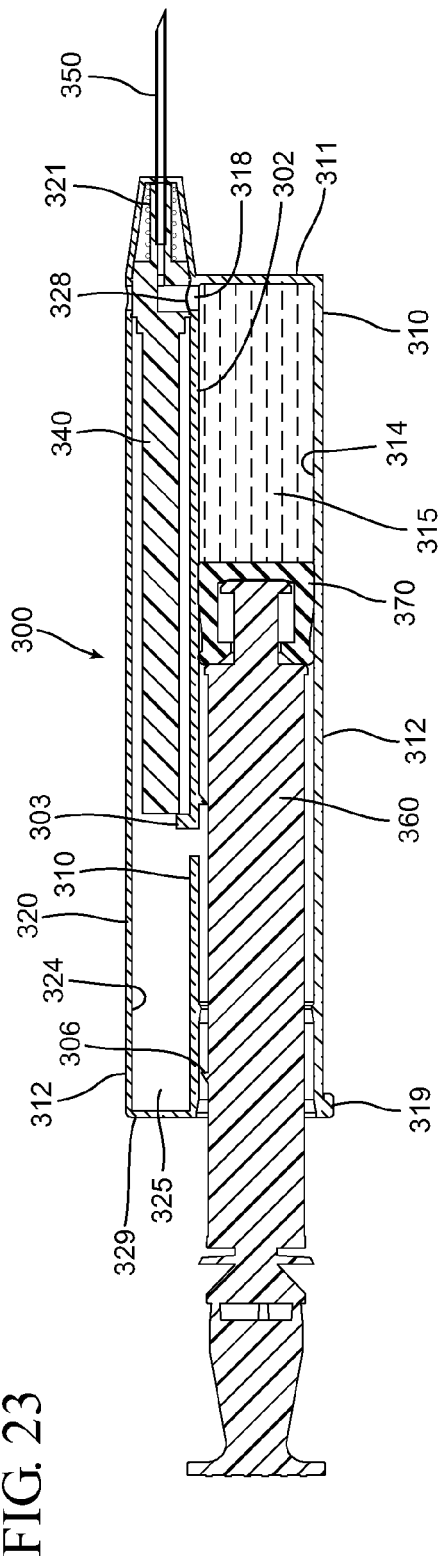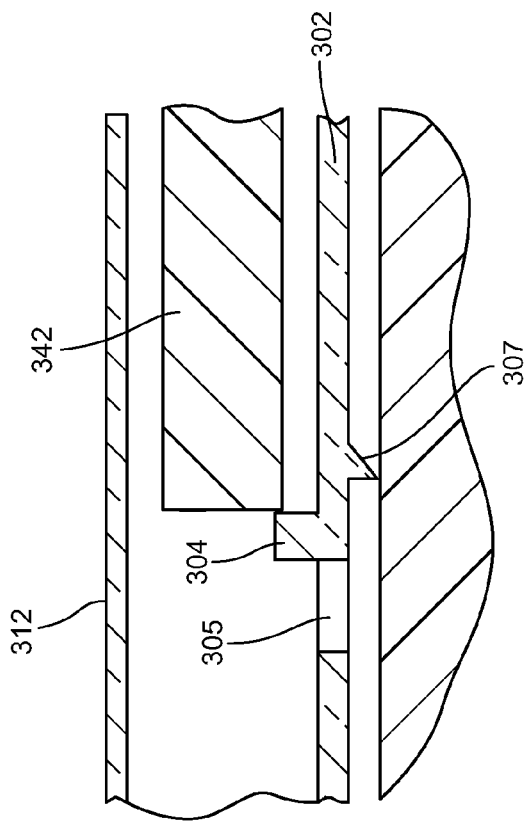
FIG. 23
FIG. 23A

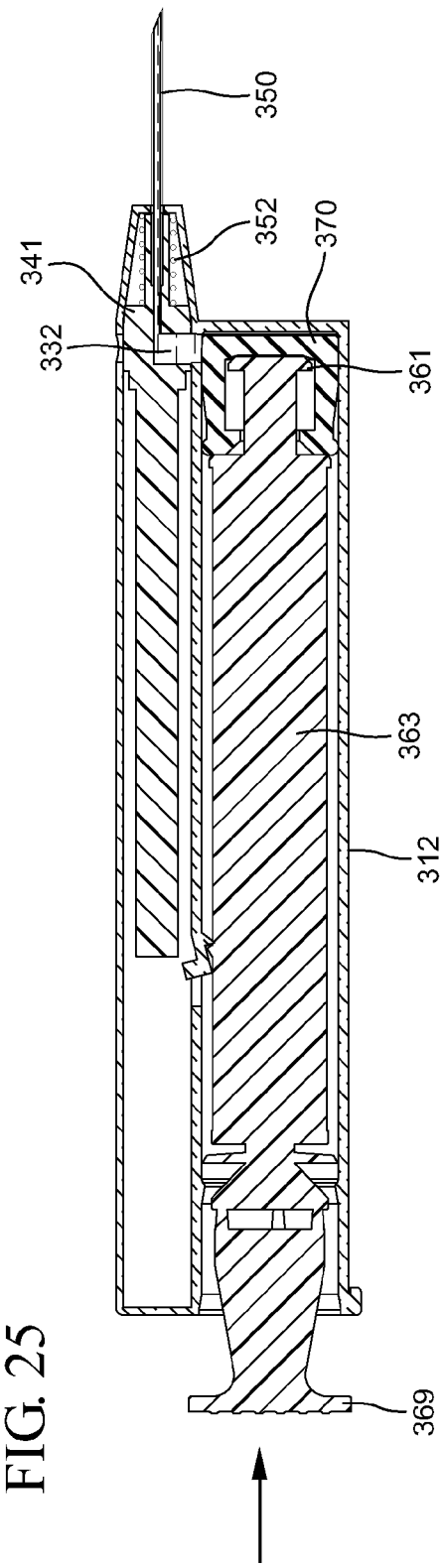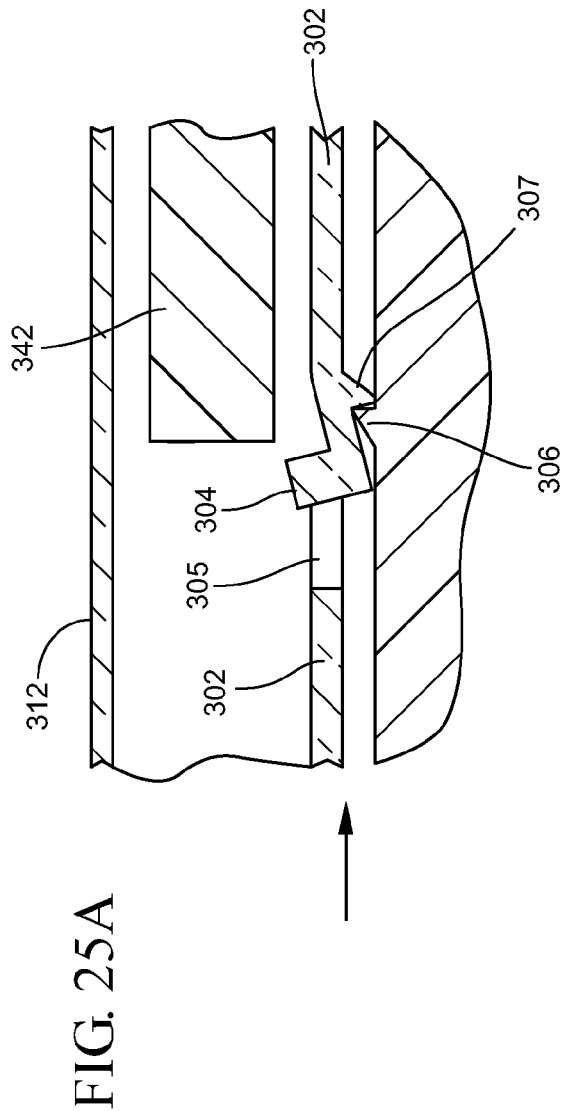
FIG. 25
FIG. 25A

DUAL CHAMBER PASSIVE RETRACTION NEEDLE SYRINGE

CROSS-REFERENCE TO RELATED APPLICATIONS

This application claims priority under 35 U.S.C. §119(e) to U.S. Provisional Application No. 61/366,749, filed Jul. 22, 2010, the disclosures of which are incorporated herein by reference in their entirety.

TECHNICAL FIELD

Aspects of the present invention relate to syringe assemblies that include a retractable needle and reuse prevention features and methods of using such syringe assemblies.

BACKGROUND

Needle retraction features have been incorporated into syringe assemblies to protect users from needle stick injuries. In conventional assemblies, the needle hub assemblies including a needle cannula, are attached to the syringe barrel and must be withdrawn into the syringe barrel by a user or by a retraction feature. Alternatively, a needle shield may be placed over the needle cannula by the user or otherwise.

In conventional syringe assemblies in which the needle hub assemblies are retracted into the syringe barrel by a retraction feature, the retraction feature is often provided within the syringe barrel and/or the plunger rod disposed within the syringe barrel. Specifically, the plunger rod may include a chamber that houses the needle hub after it is retracted. The retraction feature typically includes a cutting element disposed between the plunger rod and the stopper that is used to open the stopper after the contents of the syringe barrel are expelled, to expose the chamber of the plunger rod to receive the retracted needle hub. A spring is often incorporated in the needle hub assemblies to drive the retraction of the needle hub into the plunger rod.

Accordingly, such retraction features require cutting, braking, piercing or other force-intensive mechanical action for activation and, thus, increased complexity to enable the sealed plunger and stopper to be breached during activation. Further, as most conventionally designed retractable needles are activated after dosing by continued pressure on the rear of the plunger rod, inadvertent activation of the retraction feature may occur since the same forces must be applied when expelling the contents of the syringe barrel. Moreover, some devices may be inadvertently activated during dosing if sufficient pressure is generated during expulsion of the contents of the syringe, for example, when the medication is viscous and requires the user to apply additional pressure or force to the plunger rod, which exceeds the force required to activate the retraction feature. Premature activation is especially problematic in applications where high forces are applied to the plunge rod, for example, during high speed injections.

The retraction features of conventional syringe barrels that are plunger-activated must withstand increased syringe pressures and associated increase in force applied to the plunger rod, as described above. These increased forces and pressure leads to a requirement for large activation forces which could exceed the operational forces in order to prevent premature activation. Since most conventional syringe barrels employ an additional plunger motion after full dispensing, and in the same manner as the dispensing motion, a threshold force must be used to allow the user to differentiate between a fully bottomed plunger and the activation of the retraction feature. The threshold force may be difficult to ascertain and maintain separately from the force applied to the plunger rod to expel the contents of the syringe barrel. Further, proper application of the threshold force may require a user to position the syringe barrel and the needle cannula at an increased angle to the patient's skin, instead of positioning the syringe barrel and needle cannula substantially parallel to the patient's skin. The additional force required to activate the retraction feature may cause additional pressure to be generated at the stopper or other removable opening in the plunger rod, which may be sufficient to cause the stopper and/or plunger rod to malfunction.

In conventional syringe assemblies where the retraction feature and the subsequent housing of the needle hub in conventional retractable syringes are contained within the fluid path, the retraction feature and housing may cause a volume of medication to become trapped within the syringe barrel, thereby increasing waste and potentially affecting dosing accuracy. Further, a portion of the trapped medication may be expelled during the activation of the retraction feature causing splatter, if the retraction feature is activated when the needle cannula is outside of the patient, or an unintended increase in the dose administered to the patient, if the retraction feature is activated when the needle cannula is in the patient. Placement of the retraction feature within the syringe barrel may also cause trapped air to remain in the syringe barrel when purging or priming the syringe. This can lead the possibility of injected air. The size of the syringe barrel must also accommodate the retraction feature and the needle hub assembly that will be housed therein after retraction.

In syringe assemblies which do not house the retraction feature within the fluid path, the retraction feature is often disposed at a location that requires the user to change their grip of the syringe assembly to activate the retraction feature.

Conventional retraction syringe assemblies often do not incorporate reuse prevention features, and thus, the retraction mechanism may be reset so the syringe barrel may be reused. The reuse of syringe assemblies without sterilization or sufficient sterilization is believed to facilitate the transfer of contagious diseases. Further, the retraction features of conventional syringes also often require the user to actively activate the retraction mechanism. Accordingly, the chance of human error in failure to activate or properly activate the retraction mechanism can lead to continued exposure of needles.

Accordingly, it would be desirable to provide a retractable syringe assembly with a retraction feature that does not interfere with normal operation of the syringe assembly, is passively activated and reduces the risk of premature activation or the retraction mechanism. It would also be desirable to provide a retractable syringe assembly which incorporates a reuse prevention feature.

SUMMARY OF THE INVENTION

One embodiment of the present invention pertains to a syringe assembly comprising a fluid barrel including a sidewall having an inside surface defining a fluid chamber for retaining fluid and having a first cross-sectional width, an open proximal end and a distal end including a distal wall; a plunger rod disposed within the fluid chamber comprising a distal end, a proximal end, a plunger rod body extending from the distal end to the proximal end, and a stopper disposed at the distal end of the plunger rod for forming a fluid-tight seal with the inside surface of the barrel; a retraction barrel disposed adjacent to the sidewall of the fluid barrel, the retraction barrel including a wall having an interior surface defining a needle chamber, an open proximal end, an open distal end including a barrier wall, an aperture between the wall of the fluid barrel and the sidewall of the fluid barrel such that the fluid chamber and the needle chamber are in fluid communication and a needle hub assembly comprising a needle hub, a needle cannula attached to the needle hub in fluid communication with the aperture, the needle hub assembly biased to move in the proximal direction; and a trigger element moveable with the plunger rod and extending into the needle chamber of the retraction barrel, the trigger element providing a trigger force causing the needle cannula to retract into the retraction barrel.

In one or more embodiments of the present invention, the wall of a syringe assembly of the present invention includes a supporting element that engages a needle assembly disposed within the needle chamber and the supporting element is positioned to apply a force in the distal direction to the needle hub such that the needle cannula extends distally beyond the open distal end of the retraction barrel in first position.

In one or more embodiments of the present invention, the trigger element provides a trigger force on the needle hub to disengage the supporting element and the needle hub so the needle cannula is housed within the retraction barrel.

In one or more embodiments of the present invention, the needle hub is biased by a spring disposed between the needle hub and the barrier wall that exerts a force on the needle hub in the proximal direction.

In one or more embodiments of the present invention, the trigger element is attached to the distal end of the plunger rod. In one or more embodiments of the present invention, the trigger element may include a proximal end attached to the proximal end of the plunger rod, a free and open distal end that provides the trigger force, and a trigger element body extending from the proximal end to the distal end and including an interior surface defining a hollow interior.

In one or more embodiments of the present invention, the inside surface of the syringe barrel includes a retaining ring adjacent said proximal end defining a second cross-sectional width that is less than the first cross-sectional width and the plunger rod body includes a flexible protrusion having a cross-sectional width greater than the cross-sectional width of the barrel at the rib and a frangible portion.

In one or more embodiments of the present invention, the plunger rod body comprises a distal portion and a proximal portion, the protrusion disposed between the distal portion and the proximal portion. In one or more embodiments of the present invention, the distal portion of the plunger rod body comprises a support member disposed proximally adjacent to the flexible protrusion and at least one frangible portion disposed proximally adjacent to the support member. In one or more embodiments of the present invention, the proximal end of the trigger element is attached to the thumbpress of the plunger rod. In one or more embodiments of the present invention, the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when the distal end of the stopper is in contact with the distal wall of the barrel, the protrusion is permitted to advance distally past the rib in the barrel and lock the plunger rod in the barrel to prevent reuse of the syringe assembly. In one or more embodiments of the present invention, the stopper-engaging portion of the plunger rod is connected to the stopper such that upon application of an initial proximally directed force to the plunger rod, while holding the barrel, causes the plunger rod and the trigger element to move the length of the axial distance in a proximal direction within the barrel, while the stopper remains stationary. In one or more embodiments of the present invention, the stopper-engaging portion of the plunger rod is connected to the stopper such that upon application of a continuous proximally directed force to the plunger rod, while holding the barrel, causes the stopper, the plunger rod and the trigger element to move together in a proximal direction within the barrel. In one or more embodiments of the present invention, the stopper-engaging portion of the plunger rod is connected to the stopper such that application of an initial distally directed force to the plunger rod after application of a proximally directed force to the plunger rod, while holding the barrel, causes the stopper to remain stationary and the plunger rod and the trigger element to move the length of the axial distance in the distal direction within the barrel. In one or more embodiments of the present invention, the stopper-engaging portion of the plunger rod is connected to the stopper such that application of a continuous distally directed force to the plunger rod causes the stopper, plunger rod and the trigger element to move together in the distal direction within the barrel until the stopper reaches the distal end of the barrel. In one or more embodiments of the present invention, contact between the stopper and the distal wall of the barrel causes the support element to disengage from the needle hub and the protrusion to advance distally past the rib in the barrel and lock the plunger rod in the barrel to prevent reuse of the syringe assembly. In one or more embodiments of the present invention, application of a proximally directed force to the plunger, after the protrusion has advanced distally past the rib, causes the at least one frangible portion of the plunger rod to break. In one or more embodiments of the present invention, application of a continuous proximally directed force on the plunger rod causes the stopper-engaging portion to disengage from the stopper.

In one aspect of the present invention, the open distal end of the trigger element comprises a beveled edge that extends distally.

In one or more embodiments of the present invention, the retraction barrel is disposed parallel to the fluid barrel.

Another embodiment of the present invention pertains to syringe assembly comprising a barrel comprising including an open proximal end, sidewall having an inside surface defining a fluid chamber for retaining fluid and having a first cross-sectional width and a needle chamber for housing a needle hub assembly, the fluid chamber and the needle chamber being divided by a barrier wall having a first aperture permitting fluid communication between the fluid chamber and the needle chamber, the needle chamber including a flexible tab that extends into the needle chamber to engage a needle hub assembly disposed therein; a needle hub assembly disposed within the needle chamber, the needle hub assembly comprising a needle hub, a needle cannula attached to the needle hub in fluid communication with the first aperture, the needle cannula biased to move in the proximal direction, the flexible tab positioned to engage the needle hub and apply a force in the distal direction to the needle hub so that the needle cannula extends beyond the open distal end of the retraction barrel in a positioned in first position; and a plunger rod disposed within the fluid chamber comprising a distal end, a proximal end, a stopper disposed at the distal end of the plunger rod for forming a fluid-tight seal with the inside surface of the barrel, a plunger rod body extending from the distal end to the proximal end, and an activation element disposed on the plunger rod to move the flexible tab and cause the needle cannula to retract and be housed within the retraction barrel in a second position.

In one or more embodiments of the present invention, the needle cannula is biased to move in the proximal direction by a spring disposed between the needle hub and the barrier wall that exerts a force on the needle hub and the spring is compressed when the flexible tab engages the needle hub. In one or more embodiments of the present invention, the needle chamber barrier wall further comprises a second aperture to permit the flexible tab to flex inwardly into the needle chamber and a ramped portion that extends outwardly into the fluid chamber. In one or more embodiments of the present invention, the disengagement of the flexible tab and the needle hub permits the spring to expand and causes the needle hub to retract into the hollow interior of the trigger element.

In one or more embodiments of the present invention, the trigger element is disposed on the plunger rod body and extends radially outwardly from the plunger rod body. In one or more embodiments of the present invention, the barrel comprises a dose limit indicator disposed on an outside surface of the sidewall. In one or more embodiments of the present invention, upon application of a force in the proximal direction on the plunger rod causes the plunger rod to move in the proximal direction and aspirate a liquid into the fluid chamber and the sequential application of a force in the distal direction causes the plunger rod to engage the ramp and cause the flexible tab to flex outwardly into the fluid chamber to release the force applied to the needle hub in the distal direction. the inside surface of the side wall at the fluid chamber includes a retaining ring adjacent said proximal end defining a second cross-sectional width that is less than the first cross-sectional width and the plunger rod body includes a flexible protrusion having a cross-sectional width greater than the cross-sectional width of the barrel at the rib and a frangible portion.

In one or more embodiments of the present invention, the contact between the stopper and the distal wall of the barrel causes the flexible tab to disengage from the needle hub and the protrusion to advance distally past the rib in the barrel and lock the plunger rod in the barrel to prevent reuse of the syringe assembly. In one or more embodiments of the present invention, the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly.

Yet another embodiment of the present invention pertains to a syringe assembly comprising a fluid barrel including a sidewall having an inside surface defining a fluid chamber for retaining fluid and having a first cross-sectional width, an open proximal end and a distal end including a distal wall; a plunger rod disposed within the fluid chamber comprising a distal end, a proximal end, a plunger rod body extending from the distal end to the proximal end, and a stopper disposed at the distal end of the plunger rod for forming a fluid-tight seal with the inside surface of the barrel; a retraction barrel disposed adjacent to the sidewall of the fluid barrel, the retraction barrel including a wall having an interior surface defining a needle chamber, an open proximal end, an open distal end including a barrier wall, an aperture between the wall of the fluid barrel and the wall of the fluid barrel such that the fluid chamber and the needle chamber are in fluid communication and a needle hub assembly comprising a needle hub, a needle cannula attached to the needle hub in fluid communication with the aperture, the needle hub assembly biased to move in the proximal direction; and a retraction mechanism to the needle cannula to retract into the retraction barrel, wherein the retraction barrel is nested with the fluid barrel and the retraction barrel has cross-sectional dimension that is less than 90% of the cross-sectional dimension of the fluid barrel.

BRIEF DESCRIPTION OF THE DRAWINGS

FIG. 8 illustrates a cross-sectional view of the syringe assembly of FIG. 7 after a force in the distal direction has been applied to the plunger rod to expel the liquid from the fluid chamber;

FIG. 9 illustrates a cross-sectional view of the syringe assembly of FIG. 8 after all of the liquid has been expelled from the fluid chamber and the stopper is in contact with the distal wall;

FIG. 11 illustrates a cross-sectional view of the syringe assembly of FIG. 10 after a force is applied on the plunger rod in the proximal direction, after the plunger rod is locked within the fluid barrel;

FIG. 23 illustrates a cross-sectional side view of a retractable syringe assembly according to one or more embodiments, with fluid filled in the fluid chamber;

FIG. 25 illustrates a cross-sectional side view of a retractable syringe assembly shown in FIG. 24 after the fluid is expelled from the fluid chamber;

DETAILED DESCRIPTION

Figure 1:
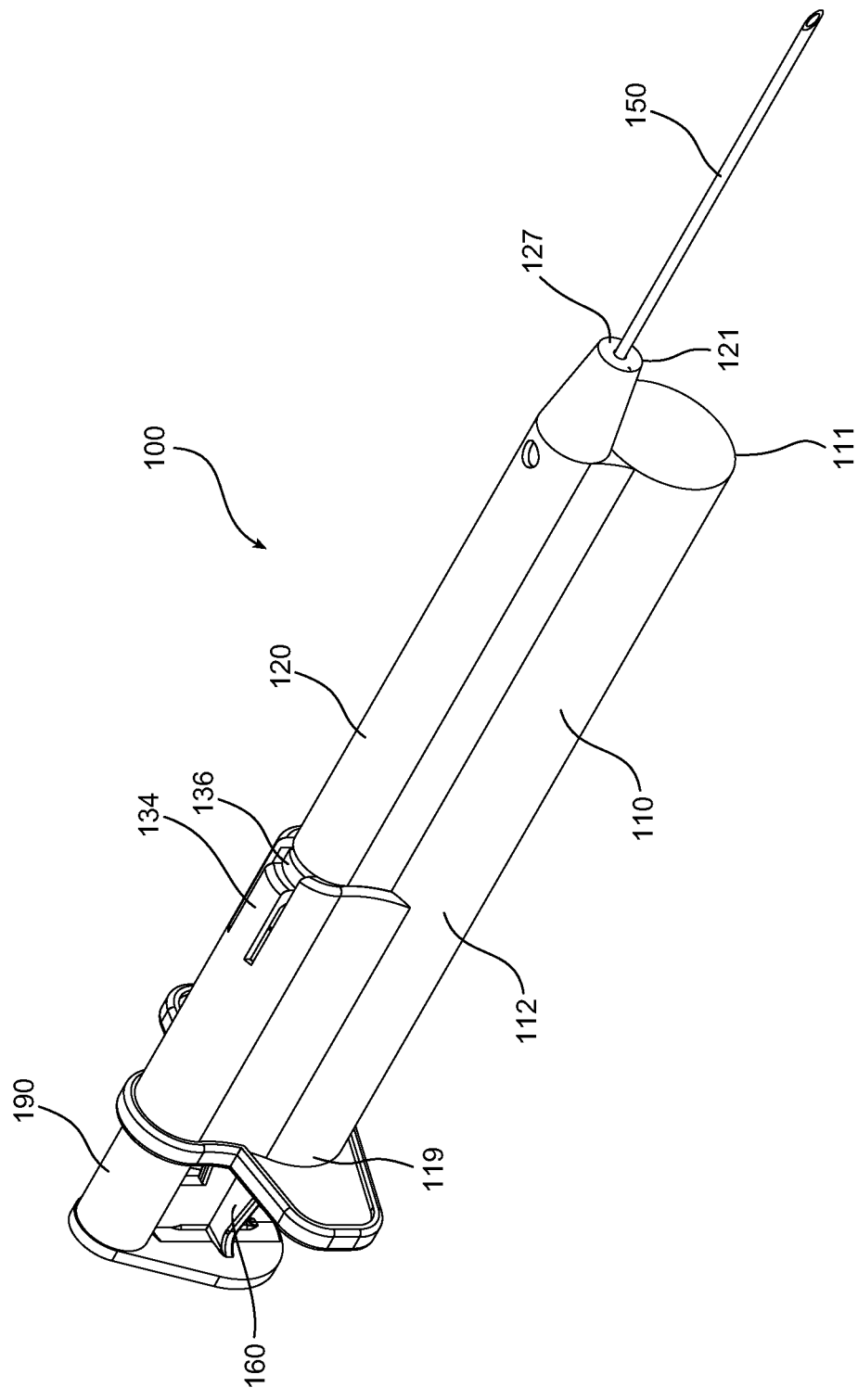
FIG. 1 illustrates a perspective view of a retractable syringe assembly according to one or more embodiments.
Figure 2:
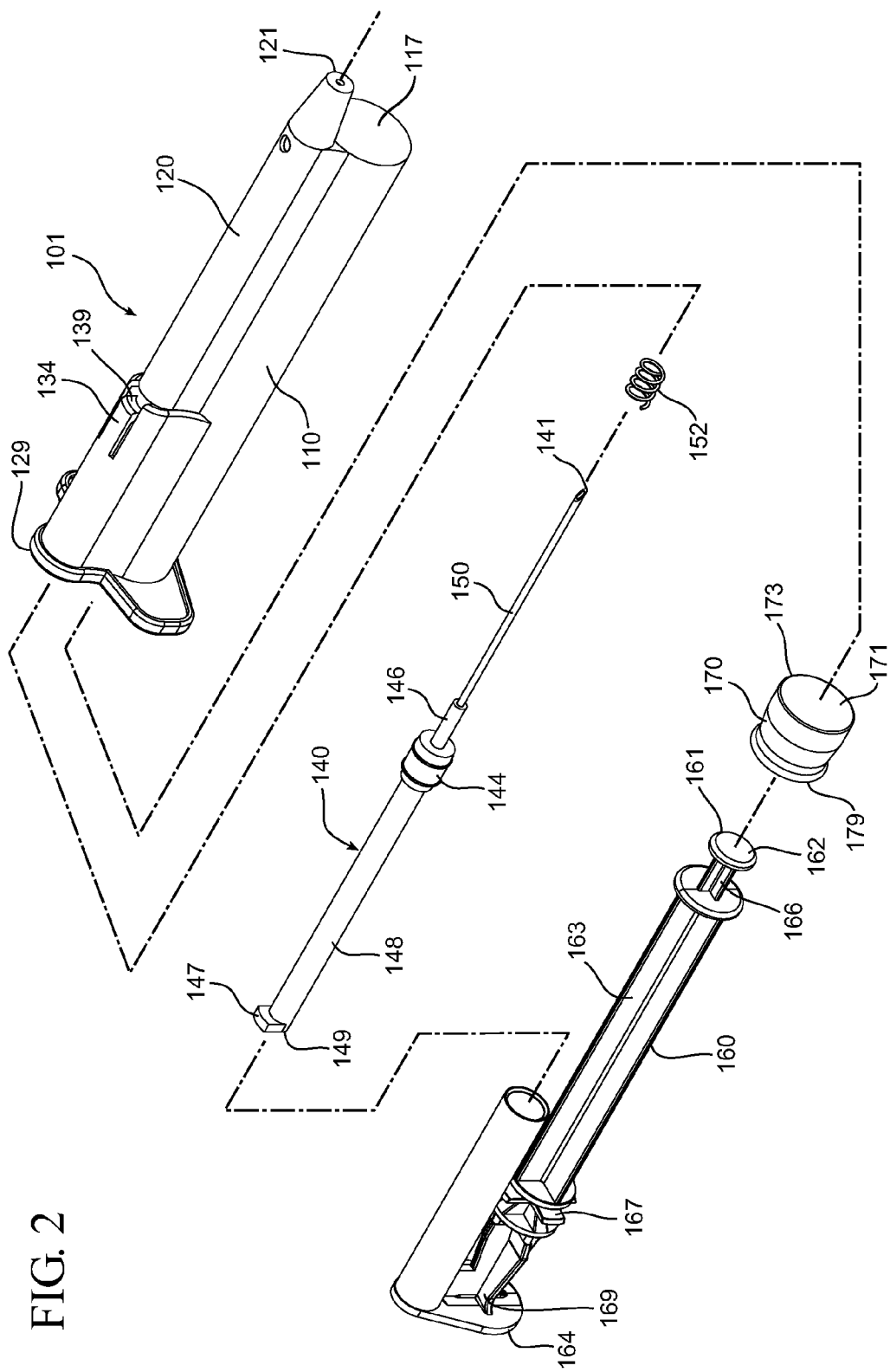
FIG. 2 illustrates an exploded view of the syringe assembly of claim 1.
Figure 3:
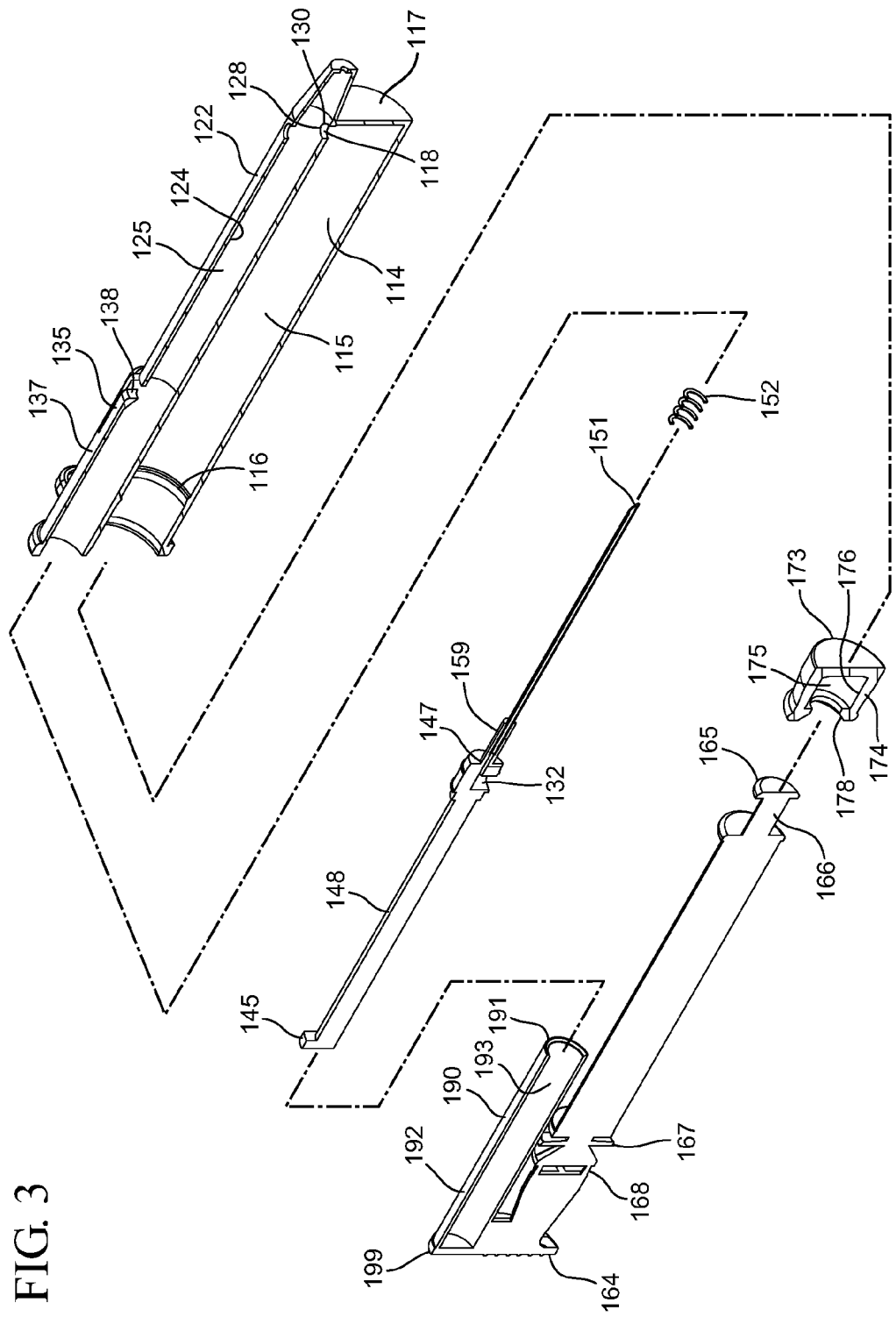
FIG. 3 illustrates a cross-sectional view of the syringe assembly of claim 2.

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

A first aspect of the present invention pertains to a retractable syringe assembly having a passive retraction feature. The retractable syringe assembly 100 of one or more embodiments utilizes a dual syringe barrel or a syringe barrel that isolates the fluid chamber from the retraction feature.

In the embodiment shown in FIGS. 1-11, the retractable syringe assembly includes a dual syringe barrel 101 that includes fluid barrel 110 and a retraction barrel 120. The retractable syringe also includes a needle hub assembly 140, a plunger rod 160, stopper 170 and a trigger element 190. The fluid barrel shown in FIG. 4, includes a distal end 111, a open proximal end 119, a sidewall 112 extending from the distal end 111 and the proximal end 119 including an inside surface 114 defining a chamber 115. The inside surface 114 defines a cross-sectional width and may include a reuse prevention feature, that will be discussed in greater detail below. The distal end 111 includes a distal wall 117 that encloses the distal end 111. In the embodiment shown, the sidewall 112 includes a first aperture 118 for permitting fluid communication between the fluid barrel and the retraction barrel. As will be discussed in greater detail below, the first aperture 118 also permits fluid communication between a needle cannula disposed within the retraction barrel 120 and the fluid barrel 110.

Figure 4:
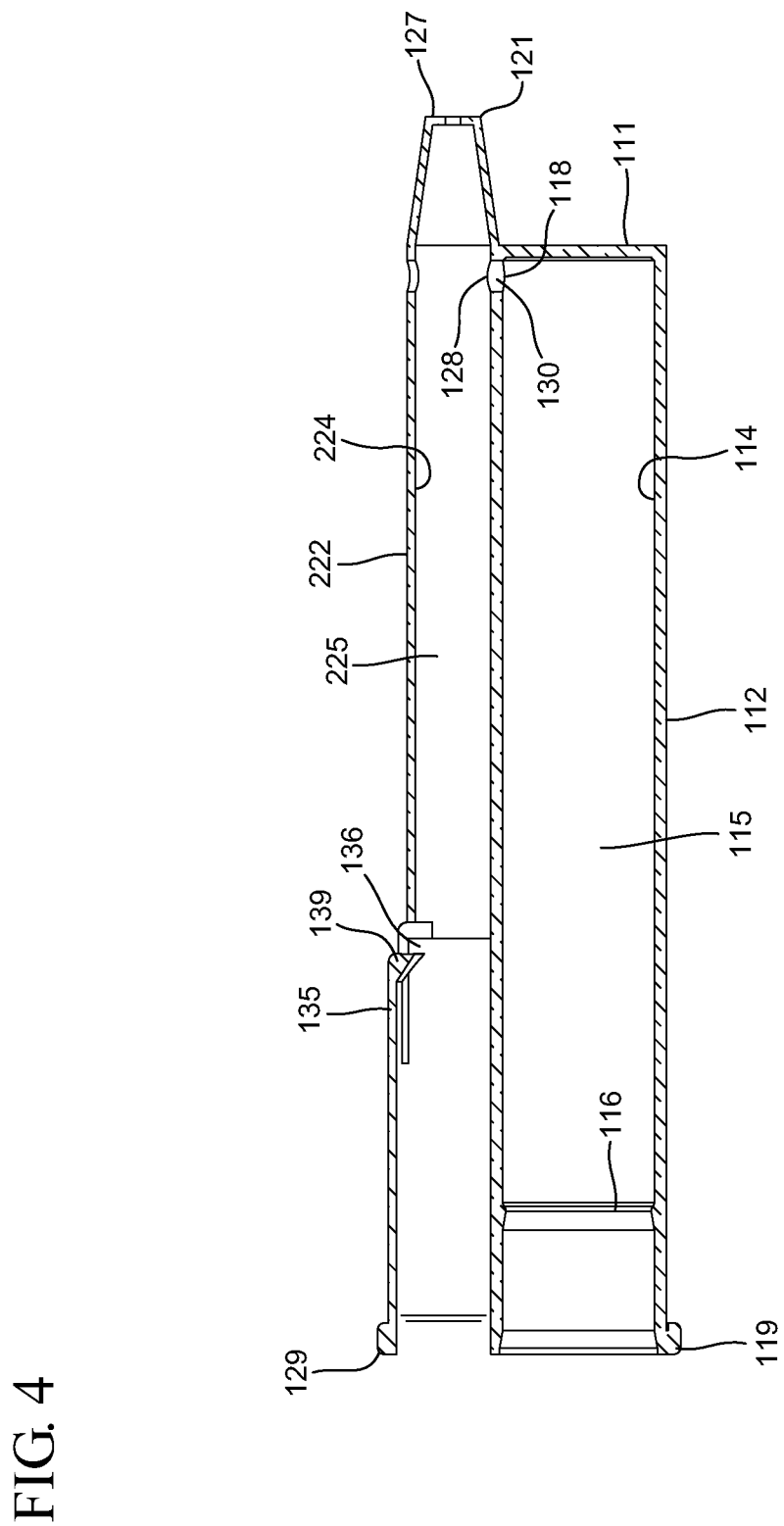
FIG. 4 illustrates a cross-sectional side-view of the fluid barrel and the retraction barrel shown in FIG. 1.

The fluid barrel 110 shown in FIG. 4, include a reuse prevention feature. Specifically, the fluid barrel 110 includes a retaining element 116 shown in the form of a rib that extends around the entire circumference of the inside surface 114 of the fluid barrel 110 at a location adjacent to the proximal end 119 of the fluid barrel. The cross-sectional width of the inside surface 114 at the retaining element 116 is less than the first cross-sectional width or the cross-sectional width of the inside surface 114 at the remaining locations along the length of the fluid barrel. In one or more embodiments, optional tabs or detents can be used to create a region of the fluid barrel 110 having a cross-sectional width that is less than the first cross-sectional width of the fluid barrel 110. The retaining ring 116 may also be shaped to facilitate activation of the reuse prevention feature. For example, the fluid barrel 110 may also include a diameter transition region disposed proximally adjacent to the retaining element 116 at the proximal end 119 of the fluid barrel 110. The cross-sectional width of the inside surface 114 of the fluid barrel at the diameter transition region increases from the distal end 111 to the proximal end 119 of the fluid barrel 110. As will be described in greater detail below, in embodiments of the retractable syringe assembly that utilize a reuse prevention feature, the reuse prevention feature of the fluid barrel 110 cooperates with corresponding reuse prevention features on the plunger rod 160 to lock the plunger rod 160 within the fluid barrel 110 and/or to disable the plunger rod 160 from further use.

In an alternative embodiment, the retractable syringe assembly may include a single barrel, wherein a portion of the barrel is divided by a dividing wall into a fluid barrel and the remaining portion of the barrel that houses the retraction feature and the needle hub assembly. The dividing wall may include an aperture for permitting fluid communication between the fluid barrel and the remaining portion of the barrel that houses the retraction feature and the needle hub assembly.

The retraction barrel 120 is disposed adjacent to the sidewall 112 of the fluid barrel 110 in the embodiment shown in FIG. 4. The retraction barrel 120 is configured to house a needle hub assembly 140 therein and the retraction feature. The retraction barrel 120 includes an open distal end 121 and an open proximal end 129. A wall 122 having an interior surface 124 defining the needle chamber 125 extends from the open distal end 121 to the open proximal end 129. The wall 122 of the retraction chamber is adjacent to the sidewall 112 of the fluid barrel 110. In one or more embodiments, the wall 122 may extend around the portions of the retraction barrel 120 that are not in direct contact with fluid barrel 110 and the sidewall 112 may form the barrier between the retraction barrel 120 and the fluid barrel 110. In other words, the outside surface of the sidewall 112 may form the interior surface 124 of the retraction barrel 120 along the portion of the retraction barrel 120 that is in direct contact with the fluid barrel 110.

The size of the needle chamber 125 may be modified to accommodate the needle hub assembly 140 and/or the retraction feature. According to one or more embodiments, the interior surface 124 of the retraction barrel 120 has a cross-sectional width that is smaller than the first cross-sectional width of the fluid barrel 110. In specific embodiments, the cross-sectional width of the interior surface 124 of the retraction barrel is less than about 90%, 80%, 70%, 60%, 50%, 40%, 30%, or 20% of the cross-sectional width of the inside surface 114 of the fluid barrel. Such designs in which the cross-sectional width of the interior surface 124 of the retraction barrel is less than the cross-sectional width of the inside surface 114 of the fluid barrel, provides ergonomic and functional advantages. For example, the overall appearance and handling of the dual barrel syringe is more appealing to the user. In certain embodiments, the retraction barrel can be nested within the fluid barrel. For example, both the retraction barrel and the fluid barrel may both be bounded or circumscribed by a common wall, and the retraction barrel may be partially or fully disposed within the fluid barrel, or alternatively, a dividing wall may separate a single barrel into two separate barrels, a fluid barrel and a retraction barrel.

The open distal end 121 of the retraction barrel 120 in the embodiment shown includes a barrier wall 127 that partially encloses the open distal end 121. The open distal end 121 may be free of a barrier wall 127 and may be fully open. The wall 122 may include a second aperture 128 that permits fluid communication with the fluid chamber 115 and the needle chamber 125. The second aperture 128 of the wall may also allow fluid communication between the fluid chamber 115, needle chamber 125 and the needle cannula. The fluid communication between the fluid barrel 110 and retraction barrel 120 may be provided by a first conduit 130 that extends from a first aperture 118 of the fluid barrel 110 and the second aperture 128 of the retraction barrel. In the embodiment shown, the first conduit 130 extends along the width of the sidewall 112 and the wall 122.

The needle hub assembly may include a second conduit 132 that extends from an open end of the needle cannula to second aperture 128 of the retraction barrel. The second conduit 130 may include an opening 133 that must be aligned with the second aperture 128 to permit fluid communication between the needle cannula and the fluid barrel.

Figure 6:
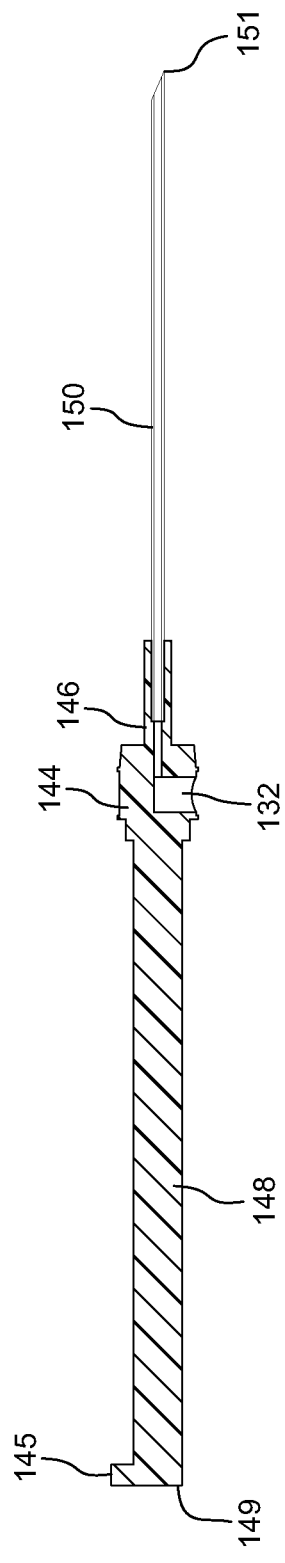
FIG. 6 illustrates a cross-sectional side-view of the needle hub assembly in FIG. 1.
Figure 6A:
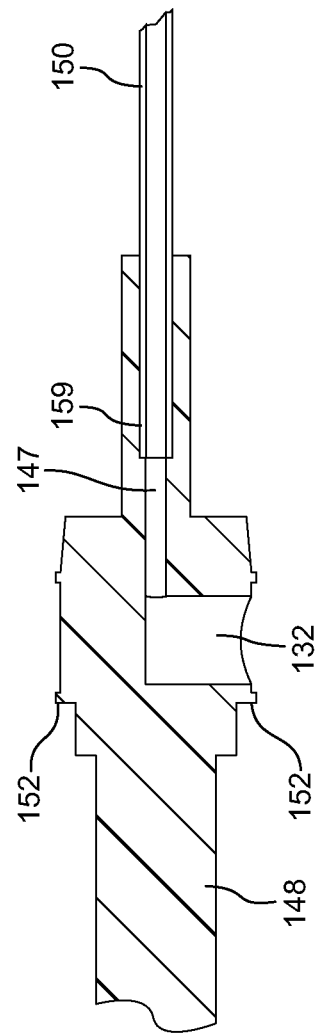

The needle hub assembly 140 is disposed within the retraction barrel 120 and includes a needle hub 142 and a needle cannula 150 attached to the needle hub 142. The needle hub 142 includes a distal end 141 and a proximal end 149. The needle cannula 150 includes a free and open distal end 151 and an open proximal end 159 that is attached to the distal end 141 of the needle hub. The needle hub 142 shown in FIG. 6 includes a needle hub body 144, a needle hub support 146 disposed distally adjacent to the needle hub body and a needle hub extension 148 that extends in the proximal direction from the needle hub body 144. The needle hub support 146 includes a recessed portion 147 for partially housing the proximal end 159 of the needle cannula. In the embodiment shown, the recessed portion 147 includes a portion of the second conduit 132 that extends through the needle hub 142 to the second aperture 128 of the retraction barrel. In one or more alternative embodiments, the proximal end 159 of the needle cannula may extend through the recessed portion 147 to the second conduit 132, which is located fully within the needle hub body 144 and does not extend into the needle cannula support 146. The needle hub extension 148 extends into the needle chamber 125 and forms part of the retraction feature of the retractable syringe assembly 100. The needle hub extension 148, as shown in FIG. 6, is provided in the form of an elongate rod that is cylindrical in shape. However, the needle hub extension may have other shapes. The needle hub extension 148 includes a latch portion 145 that extends radially outwardly from the needle hub extension 148.

The needle cannula 150 of the needle hub assembly 140 is biased to move in the proximal direction. In the embodiment shown, the needle hub assembly 140 is biased to move in the proximal direction, thereby biasing the attached needle cannula 150. In the embodiment shown, the needle hub assembly 140 is biased to move in the proximal direction by a biasing element 152 disposed between the needle hub 142 and the barrier wall 127 of the retraction barrel 120. The biasing element 152 may include a spring 153, which may be a compression spring that applies a constant force on the needle hub 142 in the proximal direction. In alternative embodiments, the biasing element 152 may be provided in another form, for example, a lever arm (not shown) may be disposed between the needle hub and the barrier wall. The retraction barrel 120 includes a supporting element 134 that prevents the needle hub from moving in the proximal direction. As will be explained in greater detail below, the release of the supporting element 134 will allow the biased needle hub 142 and the needle cannula 150 attached thereto to retract into the retraction barrel 120. In one or more variants, a portion of the needle hub 142 may be biased. For example, the needle cannula support 146 and the needle hub extension 148 may be provided as separate components from the needle hub body 144 and may be biased such that when the support element 134 is released, the needle hub extension 148 and the needle cannula support 146 may be retracted with the needle cannula 150 into the retraction barrel 120, while the needle hub body 144 remains stationary.

The needle hub assembly is sized moveable within the needle chamber. The size and shape of the needle hub assembly may be modified to permit movement in needle chambers having different sizes. In the assembled state, prior to use, the needle hub assembly is positioned at the open distal end of the retraction barrel.

The wall 122 of the retraction barrel 120 includes the supporting element 134 that engages at least a portion of the needle hub assembly 140 or interacts with the needle hub assembly 140 to provide a force in the distal direction to the needle hub assembly 140 such that the needle hub assembly 140 is positioned at the open distal end 121 of the retraction barrel. Specifically, the needle hub assembly 140 is positioned so the needle cannula 150 extends beyond the open distal end 121 of the retraction barrel in a first position. In the first position, the supporting element 134 provides a force on the needle hub 142 in the distal direction that is greater than the force applied to the needle hub 142 in the proximal direction by the biasing element 152. The supporting element 134 in the embodiment shown is provided in the form of a flexible arm 135 that is attached to the wall 122 of the retraction barrel. The wall 122 includes an opening 136 that permits the flexible arm 135 to flex outwardly. In the embodiment shown, the flexible arm 135 includes a distal end 137 that is attached to the wall 122 and a free proximal end 138 including a tab 139 that extends radially inwardly into the needle chamber 125. The tab 139 supports the proximal end 149 of the needle hub by engaging the latch portion 145. The tab 139 and the flexible arm 135 are sized and shaped to engage the latch portion 145 and support the needle hub 142 and the needle cannula 150. The tab 139 and the flexible arm 135 are also sized and shaped to compress the biasing element 152 so the needle hub assembly is positioned in the first position. To retract the needle cannula 150 into the retraction barrel 120, as will be described in greater detail below, the flexible arm 135 is moved to release the latch portion 145. In other words, the flexible arm 135 is moved to a position in which the tab 139 can no longer support the needle hub extension 148 and apply a force on the needle hub extension 148 or needle hub 142 in the distal direction that is greater than force applied to the needle hub 142 in the proximal direction by the biasing element 152.

In an alternative embodiment, the supporting element 134 may be provided in the form of a frangible section that extends inwardly from the wall 122 of the retraction barrel. The frangible section may include a breakable shelf that supports the needle hub assembly 140. The frangible section may break to release needle hub assembly or to no longer apply a force on the needle hub extension 148 or needle hub 142 in the distal direction that is greater than force applied to the needle hub 142 in the proximal direction by the biasing element 152.

Figure 5:
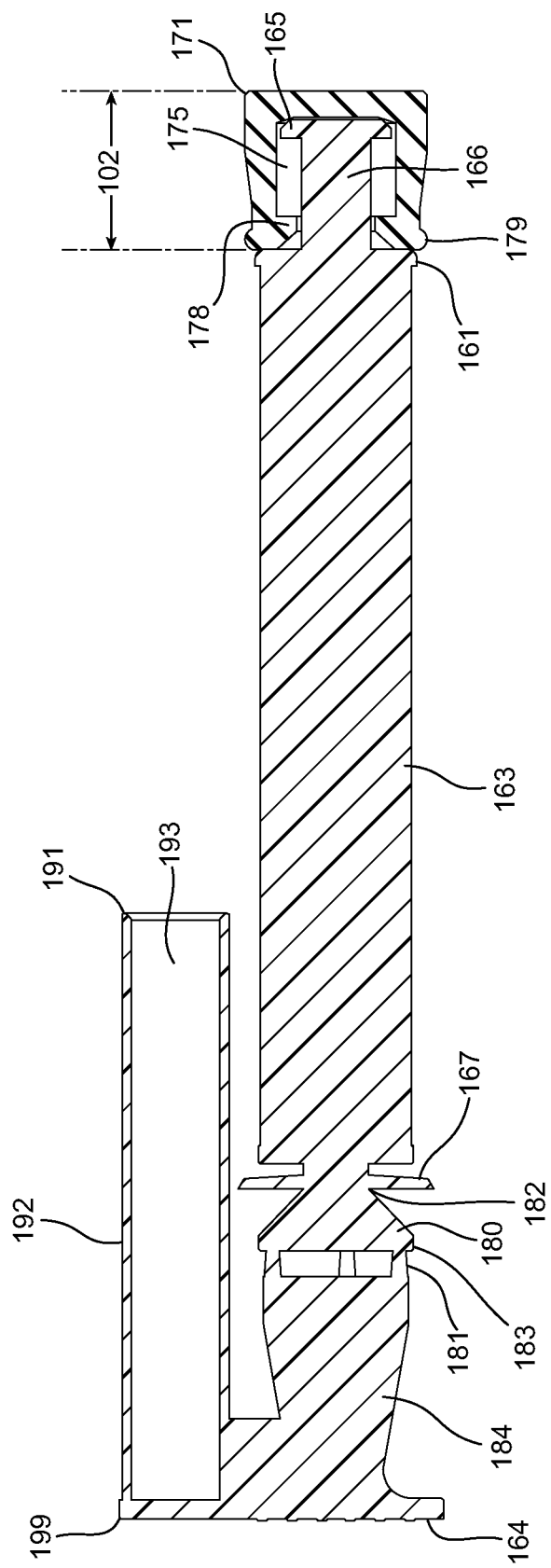
FIG. 5 illustrates a cross-sectional side-view of the plunger rod and stopper shown in FIG. 1.

A plunger rod 160 is disposed within the fluid chamber 125 and shown more clearly in FIG. 5. The plunger rod 160 includes a distal end 161 and a proximal end 169. The plunger rod 160 includes a stopper-engaging portion 162 extending from the distal end 161 to a plunger rod body 163. In one or more embodiments, the plunger rod body 163 may extend from the stopper-engaging portion 162 to the proximal end 169 of the plunger rod. In the embodiment shown in FIG. 5, the plunger rod body 163 extends from the stopper-engaging portion 162 to a reuse prevention feature that extends from the plunger rod body 163 to a thumb press 164 that is disposed at the proximal end 169 of the plunger rod. The thumb press 164 may include a thumb press support 184.

The stopper-engaging portion 162 includes an annular disc 165 disposed at the distal end of the plunger rod and a narrowed portion 166 extending from the annular disc 165 to the plunger rod body 163. The annular disc 165 engages a stopper 170 so it is disposed at the distal end of the plunge rod. In one or more embodiments, the narrowed portion 166 of the plunger rod 160 and the stopper 170 may be shaped to provide relative movement of the plunger rod 160 with respect to the stopper 170. In one or more alternative embodiments, the plunger rod 160 may be attached to the stopper 170 in a fixed relationship.

As shown in FIG. 5, the stopper 170 has a distal end 171, a proximal end 179, a stopper body 172 and a peripheral edge 173 which forms a seal with the inside surface 114 of the fluid barrel 110. In one or more embodiments, the peripheral edge 173 of the stopper 170 has cross-sectional width that permits the stopper 170 to slide in the proximal and distal directions within the fluid barrel. The stopper 170 may include an optional elongate tip (not shown) on its distal end 171 to facilitate reduction of the residual fluid and expulsion of fluid from the fluid barrel.

The stopper 170 includes a stopper body 174 extending from the peripheral edge 173 to the proximal end 179. The stopper body 174 includes a recess 175 that is defined by an inside surface 176. The recess 175 includes a neck portion 177 disposed adjacent to the proximal end 179, wherein the cross-sectional width of the inside surface 176 at the neck portion 177 is less than the cross-sectional width of the inside surface 176 at the remaining locations of the recess 175. The recess 175 allows the stopper-engaging portion 162 of the plunger rod 160 to connect to the stopper 170. The annular disc 165 engages the neck portion 177 to retain the stopper 170 on the plunger rod 160. In one or more alternative embodiments, detents (not shown) or tabs (not shown) on the stopper 170 and/or the stopper-engaging portion 162 may be used to retain the stopper 170 on the plunger rod 160.

In one or more embodiments, the cross-sectional width of the inside surface 176 may be sized and/or shaped to prevent relative movement of the stopper-engaging portion 162 within the recess 175. In the embodiment shown in FIG. 5, the cross-sectional width of the inside surface 176 of the stopper is sized and shaped to permit relative movement of the stopper-engaging portion 162 within the recess 175. Alternatively, the annular disc 165 and/or the narrowed portion 166 may be shaped and/or sized to permit or prevent relative movement of the stopper-engaging portion 162 within the recess 175.

The stopper is typically made of plastic or other easily disposable and/or recyclable material. It may be desirable to incorporate natural or synthetic rubber in the stopper or use a natural or synthetic rubber seal with the stopper. It will be understood that the stopper may incorporate multiple seals.

The retractable syringe assembly 100 also includes a trigger element 190 that includes a distal end 191 and a proximal end 199. The trigger element 190 is moveable with the plunger rod 160 but extends into the needle chamber 125 of the retraction barrel 120. In the embodiment shown, the trigger element 190 is attached to the thumb press support 184 of the plunger rod. In one or more variants, the trigger element 190 may be provided separately but configured to move with the plunger rod 160 in the distal direction when a distally directed force is applied to the plunger rod 160. In such embodiments, the trigger element 190 and the plunger rod 160 move together in the distal direction when a user applies a force on the plunger rod 160 in the distal direction.

The trigger element 190 is sized, shaped and positioned to provide a trigger force on the needle hub 142 to disengage the supporting element 134 and the latch portion 145 so the needle cannula 150 retracts and is housed into the retraction barrel. The trigger element 190 includes a trigger element body 192 that extends from the distal end 191 to the proximal end 199. The trigger element body 192 is shaped to have a cylindrical shape and is elongate. In the embodiment shown, the trigger element 190 has an open distal end 191 and the trigger element body 192 has a hollow interior 193 to house the needle hub 142 and the needle cannula 150. The proximal end 199 of the trigger element is closed and may be tapered to retain the needle hub 142 within the hollow interior 193 after the needle hub 142 and the needle cannula 150 is retracted into retraction barrel.

The open distal end 191 of the trigger element may have a beveled edge that flexes or moves the flexible arm 135 radially outwardly. The movement of the flexible arm 135 radially outwardly causes the tab 139 to also move radially outwardly so it is no longer engaging the latch portion 145 or supporting the needle hub extension 148. The movement of the tab 139 releases the force applied to the needle hub extension 148 in the distal direction by the tab 139 and, as a result, the force applied on the needle hub 142 by the biasing element 152 in the proximal direction, which remains due to the compression of the biasing element 152, causes the needle hub 142 to retract or move into the retraction barrel 120 or specifically, the hollow interior 193 of the trigger element.

Embodiments described herein utilize a passive retraction mechanism because the trigger element 190 is activated when the user applies a force on the plunger rod in the distal direction to expel the contents of the fluid barrel 110. Specifically, the trigger element 190 and the retraction feature are only activated when the full dose of medication or the entire contents of the fluid barrel 110 are expelled. Accordingly, the retraction syringe assemblies described herein are insensitive to hydraulic pressure generated during high speed injections or injections of viscous liquids from the fluid barrel, which often cause premature activation. Further, the independent retraction barrel and the housing of the retraction feature therein allows the retraction syringe barrel to have a low activation force that is based solely on the movement of the trigger element 190 in the distal direction or the application of the trigger force on the support element 134 to disengage from the needle hub 142. Accordingly, in the embodiments described herein, retraction of the needle hub 142 and needle cannula 150 does not require cutting, braking, piercing or other force-intensive mechanical action, but rather relies on the flexing of the support element 134 and the tab 139 to release the force applied to the needle hub 142 in the distal direction that counteracts the force applied to the needle hub in the proximal direction.

In the embodiment shown, the plunger rod 160 includes a reuse prevention feature. Specifically, the plunger rod 160 includes a flexible protrusion 167 disposed proximally adjacent to the plunger rod body 163 and a frangible portion 168 disposed between the flexible protrusion 167 and the thumb press 164. The plunger rod 160 may be characterized such that the plunger rod body 163 extends from the stopper-engaging portion 162 and includes a distal portion and a proximal portion wherein the flexible protrusion 167 is disposed between the distal portion and the proximal portion. The proximal portion includes the frangible portion 168.

The protrusion 167 has a cross-sectional width that is greater than the cross-sectional width of the inside surface 114 of the fluid barrel 110 at the retaining element 116. In at least one embodiment, the retractable syringe assembly is configured to allow the protrusion 167 to advance distally past the retaining element 116, to lock the plunger rod 160 in the fluid barrel 110 when the user bottoms out the plunger rod 160 in the barrel or when the stopper 170 is in contact with the distal wall 117 of the fluid barrel when all the contents of the fluid barrel 110 have been expelled. Specifically, when the plunger rod 160 is moved in the distal direction within the fluid barrel 110 upon application of a distally directed force on the plunger rod, the protrusion 167 moves distally past the retaining element 116. In the embodiment shown, movement of the protrusion 167 distally past the retaining element 116 occurs as the stopper 170 is in contact with the distal wall 117 of the fluid barrel. The smaller cross-sectional width of the inside surface 114 of the fluid barrel at the retaining element 116 prevents movement of the plunger rod 160 in the proximal direction once the protrusion 167 has moved distally past the retaining element 116. In one or more variants, the protrusion 167 may include a peripheral edge having a tapered portion (not shown) that facilitates distal movement of the protrusion 167 distally past the retaining element 116 and into the fluid barrel 110, as will become apparent in the subsequent discussion of operation of the syringe. The flexible protrusion 167 may also flex in the proximal direction as it moves distally past the retaining element 116.

In the embodiment shown, the plunger rod 160 further includes a frangible portion 168 for separating at least a portion of the plunger rod from the remaining portion of the plunger rod 160 when a user applies sufficient proximal force to the plunger rod 160 after it has been locked within the fluid barrel 110. In the embodiment shown, the frangible point 168 is located between the protrusion 167 and the thumb press 164. It will be understood that the frangible portion 168 shown is exemplary, and other suitable means for permanently damaging the plunger rod or otherwise separating at least a portion of the plunger rod from the main body may be provided. In the embodiment shown, the frangible portion 168 includes a support member 180 that extends from the flexible protrusion 167 to a plurality of point connections 181 that connect the support member 180 to the thumb press 164. The support member 180 shown in FIG. 5 has a distal end 182 and a proximal end 183. The cross-sectional width of the support member 180 increases from the distal end 182, adjacent to the flexible protrusion 167, to the proximal end 183, where the plurality of point connections 181 is disposed. The support member 180 is shown as having a circular cross-section and the plurality of point connections 181 is disposed at the peripheral edge of the proximal end 183 of the support member 180. The point connections 181 are discrete connections that form a narrowed connection point between the support member 180 and the thumb press 164. It will be understood that a single point connection 181 may also be utilized to form a narrowed connection point between the support member 180 and the thumb press 164. The thumb press support 184 may further support the thumb press and connect the plurality of point connections 181 to the thumb press 164.

In use, when the flexible protrusion 167 has advanced distally past the retaining element 116, and the user applies a force in the proximal direction on the plunger rod, the force required for the flexible protrusion 167 to overcome the retaining element 116 exceeds the force required to break the plurality of point connections 181.

In embodiments which utilize a stopper and plunger rod that permit relative movement of the plunger rod with respect to the stopper, this relative movement permits the stopper to be in contact with the distal wall 117 prior to use so that air within the fluid barrel is minimized, while still allowing the flexible protrusion to remain proximally adjacent to the retaining element and thus, allowing movement of the plunger rod in the distal and proximal directions. In this position, the annular disc 165 is disposed adjacent to the neck portion 177 of the stopper and the length of the plunger rod and stopper is maximized. In other words, in such embodiments, when the stopper 170 is attached to the stopper-engaging portion 162, and the annular disc 165 engages the neck portion 177, there is a gap between the stopper 170 and the plunger rod body 163 defining a pre-selected axial distance 102. In this position, the user may apply a force on the plunger rod in the proximal direction to draw fluid or liquid into the fluid chamber and the stopper and the plunger rod will remain in the same position with their combined length maximized. Specifically, when the user applies a force to the plunger rod 160 in the proximal direction, the plunger rod 160 and the stopper 170 move together in the proximal direction, while the stopper-engaging portion 162 is connected to the stopper 170 by the neck portion 177. In this configuration, the gap defining the pre-selected axial distance 102 is maintained while the stopper 170 and plunger rod 160 move together in the proximal direction.

Figure 7:
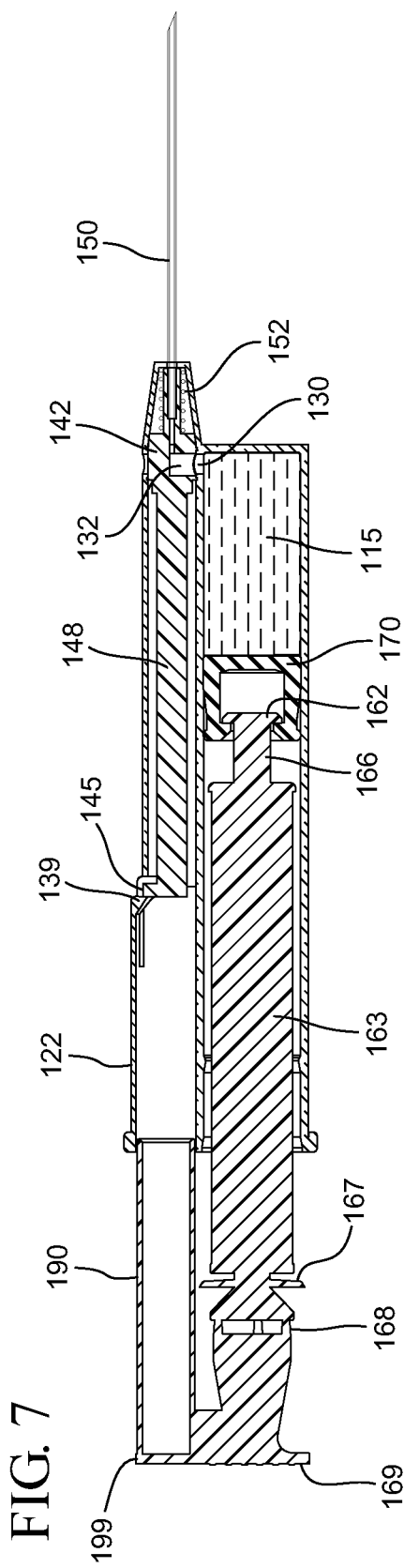
FIG. 7 illustrates a cross-sectional view of the syringe assembly of FIG. 1 after a force in the proximal direction has been applied to the plunger rod to fill the fluid chamber with liquid.
Figure 7A:
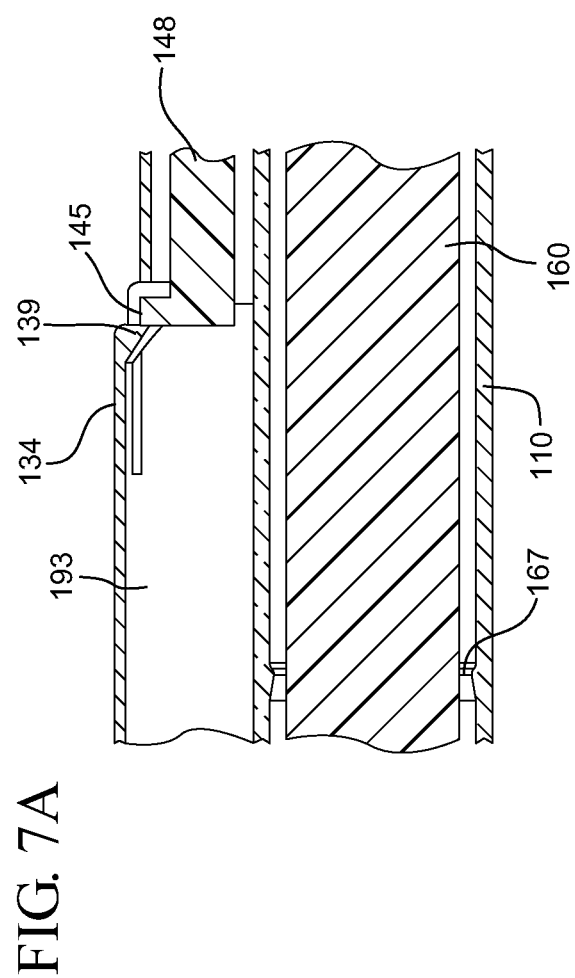

As shown in FIG. 7, the user applies proximal force to the plunger rod until a predetermined or desired amount of liquid is aspirated or drawn into the syringe. During the aspiration step, the plunger rod and the stopper body move in the proximal direction together to draw medication into the syringe, while maintaining the pre-selected axial distance 102. The trigger element 190 does not provide the trigger force and the support element 134 and the tab 139 continue to engage the latch portion 145 and support the needle hub extension 148.

When a distal force is applied to the plunger rod 160 during an injection or expulsion step to expel the contents of the fluid barrel 110 the distally-directed force closes the gap and causes the plunger rod 160 to move the pre-selected axial distance 102, while the stopper 170 remains stationary, as shown in FIG. 8. Consistent with at least one embodiment, once the stopper-engaging portion 162 has distally moved the pre-selected axial distance 102 within the recess 175, it is no longer in contact with the neck portion 177. After this relative movement of the plunger rod 160 with respect to the stopper 170, the stopper 170 and the plunger rod 160 begin to move in tandem in the distal direction. In this position, the length of the plunger rod and the stopper is shortened.

In one embodiment, the user may inject a limited amount of the fluid aspirated or exert a limited force on the plunger rod 160 in the distal direction to flush or expel some of the aspirated fluid, without locking the plunger rod 160 within the fluid barrel 110, provided that the flexible protrusion 167 remains positioned proximally adjacent to the retaining element 116. However, as will be described further below, a user will typically expel substantially all of the contents of the fluid barrel by bottoming the stopper 170 against the distal wall 117 of the fluid barrel. As the user applies a force in the distal direction to the plunger rod 160, the trigger element 190 moves within the retraction barrel 120 with the plunger rod 160, as it moves within the fluid barrel 110 in the distal direction.

Figure 10:
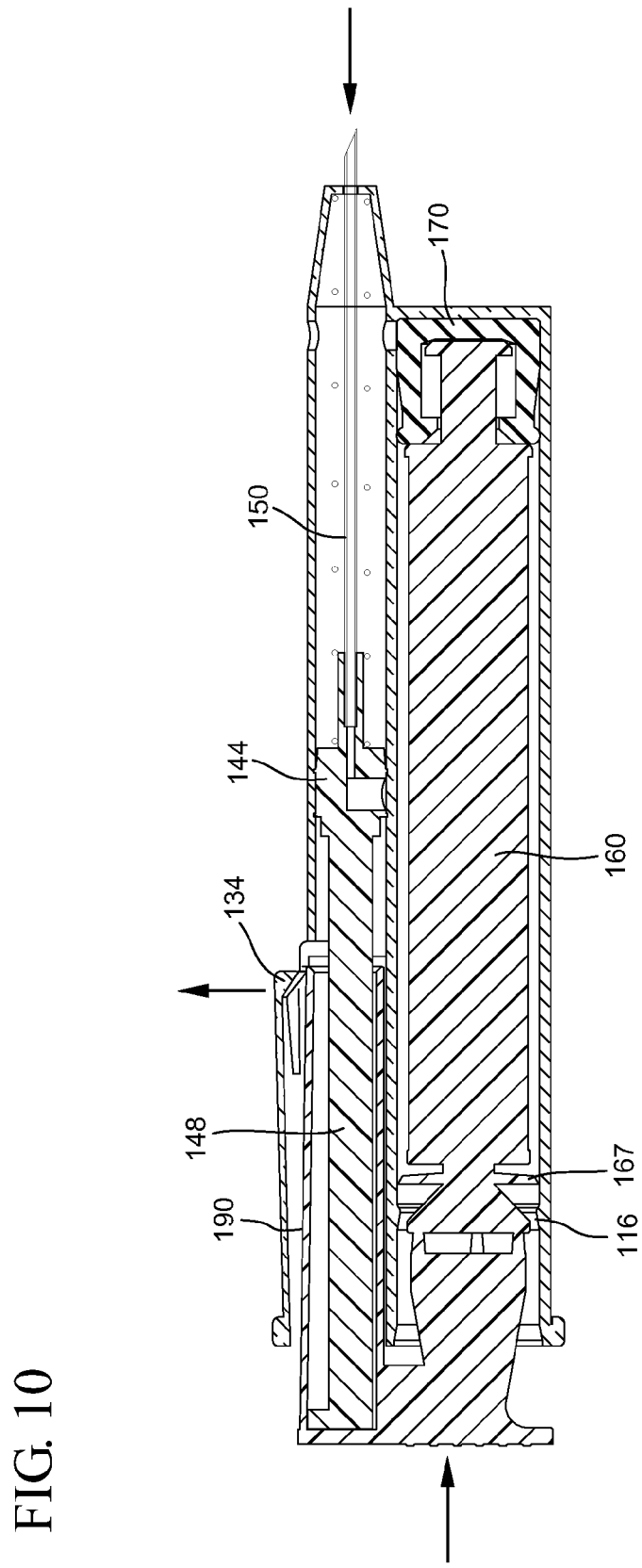
FIG. 10 illustrates a cross-sectional view of the syringe assembly of claim 9 after the needle hub assembly is retracted into the retraction barrel
Figure 12:
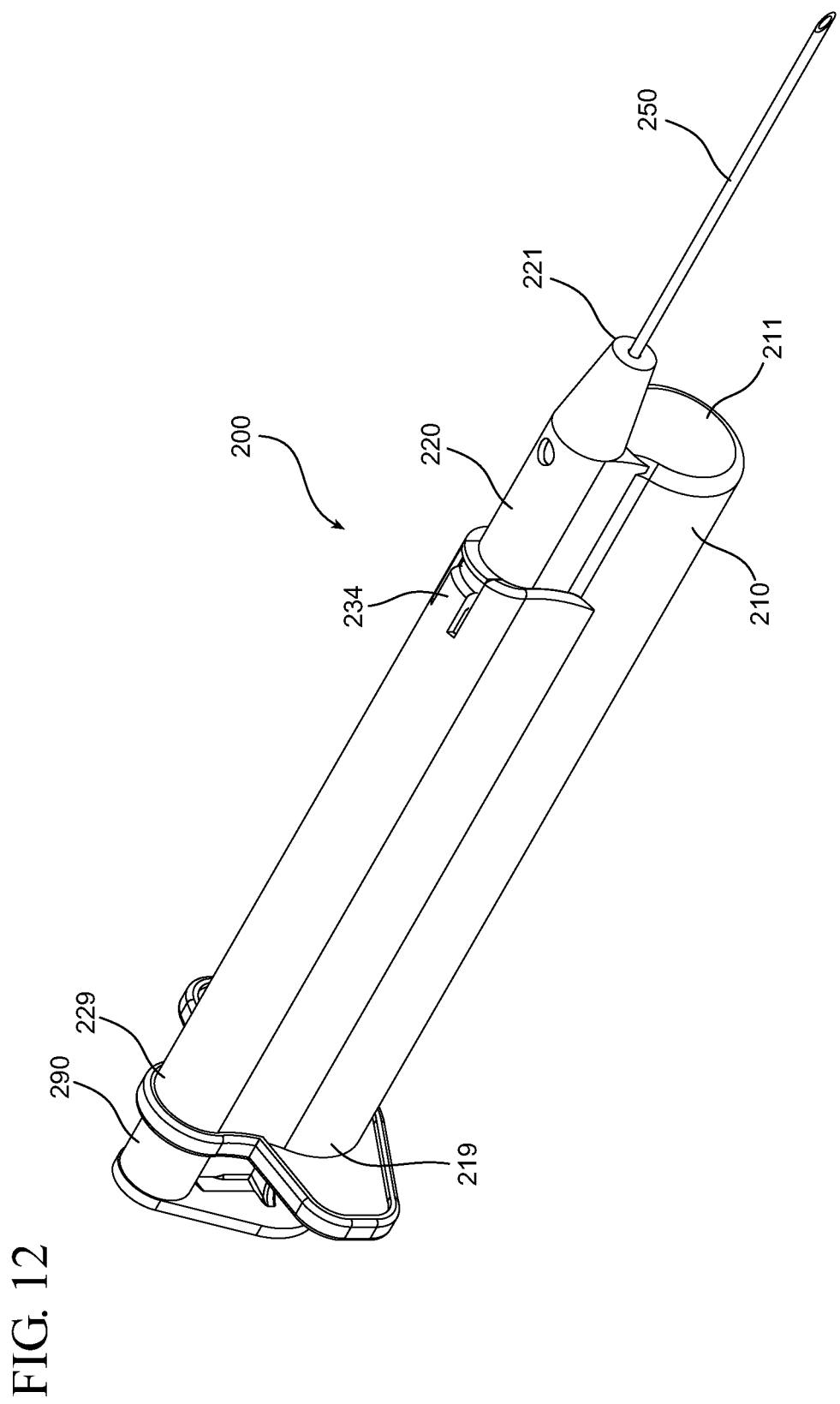
FIG. 12 illustrates a perspective view of a retractable syringe assembly according to one or more embodiments.
Figure 13:
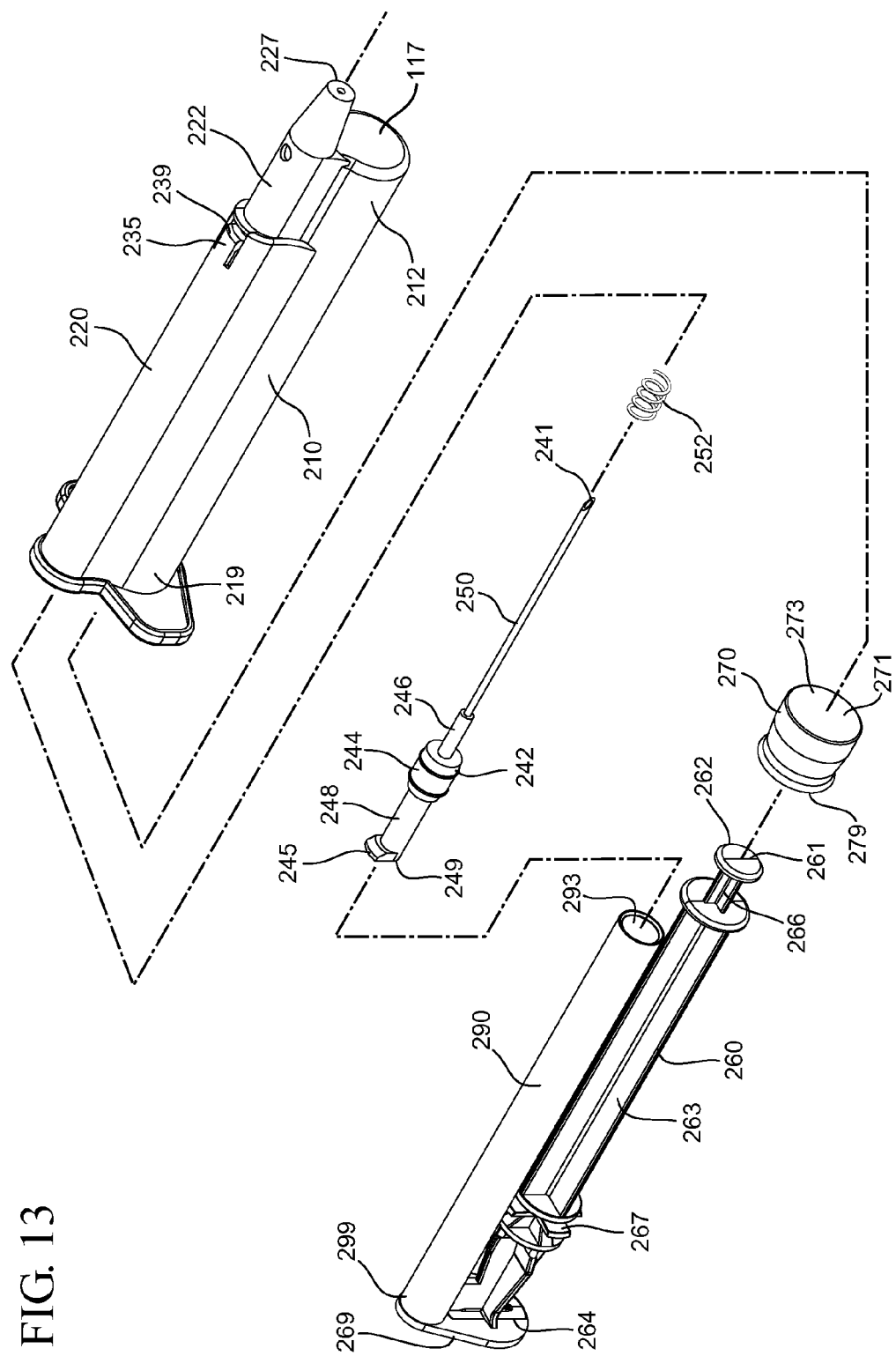
FIG. 13 illustrates an exploded view of the syringe assembly of claim 12.

As described above and shown in FIG. 9, when the stopper is in contact with the distal wall 117, the flexible protrusion 167 will have moved distally past the retaining element 116, due to the shortened length of the plunger rod 160 and the stopper 170 caused by the relative movement of the plunger rod 160 with respect to the stopper 170. The trigger element 190 applies a trigger force to the support element 134 causing the support element 134 to flex radially outwardly or to move radially outward. When the support element 134 moves radially outwardly, the tab 139 no longer applies a force to the needle hub extension 148 in the distal direction and the force applied by the biasing element 152 in the proximal direction causes the needle hub 142 and the needle cannula 150 to move into the retraction barrel 120, as shown in FIG. 10.

Referring now to FIG. 11, which illustrates the syringe assembly after the plunger rod 160 has been locked inside the fluid barrel 110, as a user attempts to reuse the retractable syringe assembly by applying a force to the plunger rod 160 in the proximal direction, the application of a proximally-directed force to the plunger rod that is greater than the force required to break the plurality of point connections 181 causes a portion of the plunger rod 160 to separate at the plurality of point connections 181. The plurality of point connections 181 breaks because the force exerted by the retaining element 116 on the flexible protrusion 167 exceeds the breaking force of the plurality of point connections 181.

As the portion of the plunger rod 160 is removed from the remaining portion of the plunger rod, as shown in FIG. 11, the needle hub assembly 140 remains within the retraction barrel 120. The needle cannula 150 is housed completely within the retraction barrel 120. The support element 134 and the tab 139 are no longer flexed because the trigger element 190 no longer applies the trigger force. In this position, the support element 134 and the tab 139 engage with a portion of the needle hub 142 that prevents removal of the needle hub and cannula from the retraction barrel. Specifically, the needle hub 142 of one or more embodiments may include a latch portion 145 that engages the tab 139 to prevent removal of the needle hub. In one or more alternative embodiments, the proximal end 199 of the trigger element 199 may have a narrowed cross-sectional portion (not shown) that engages the needle hub extension 148 such that the needle hub 142 is retained within the hollow interior 193 and the needle cannula 150 is not exposed.

In one or more embodiments, the connection between the stopper-engaging portion 162 and the stopper 170 may be frangible. For example, the peripheral edge 173 of the stopper 170 may have a cross-sectional width that is greater than the cross-sectional width of the inside surface 114 of the fluid barrel 110 at the retaining element 116. In such embodiments, after a proximally-directed force has been applied to the plunger rod 160 and the stopper 170 and the stopper 170 has moved to the proximal end 119 of the fluid barrel, the retaining element 116 engages the peripheral edge 173 of the stopper 170 and prevents the peripheral edge 173 of the stopper from moving proximally past the retaining element 116. In such embodiments, the continued application of a force in the proximal direction or the application of a proximally-directed force causes the connection between the stopper-engaging portion 162 and the stopper 170 to break. This breakage prevents a user from disassembling the parts of the retractable syringe assembly. Without being limited by theory, it is believed that the force required to break the connection between the stopper-engaging portion 162 and the stopper 170 is less than the force exerted by the retaining element 116 on the peripheral edge 173 of the stopper.

In embodiments which do not incorporate a reuse prevention feature, the user applies a force to the plunger rod 160 in the proximal direction to move the plunger rod 160 and the stopper 170 in the proximal direction. The movement of the plunger rod 160 and the stopper 170 in the proximal direction creates a vacuum within the fluid barrel 110. In this position, the trigger element 190 does not apply the trigger force to the support element 134 and the support element 134 and the tab 139 continue to apply a force on the needle hub 142 in the distal direction that is greater than the force applied to the needle hub 142 by the biasing element 152 in the proximal direction. After the desired amount of liquid is aspirated into the fluid barrel 110, the user applies a force on the plunger rod 160 in the distal direction. As the plunger rod 160 and the stopper 170 move in the distal direction, the trigger element 190 also moves with the plunger rod 160 in the distal direction. Once all of the contents of the fluid barrel 110 are expelled by the stopper and the stopper 170 is in contact with the distal wall 117, the trigger element 190 applies a trigger force on the support element 134 and moves the support element 134 and the tab 139 radially outwardly so they no longer apply a force to the needle hub 142 in the distal direction and is released. The force applied to the needle hub 142 in the distal direction is released because the support element 134 and the tab 139 are no longer supporting the needle hub extension 248. The force applied to the needle hub 142 in the proximal direction by the biasing element 152 then drives the needle hub 142 and the needle cannula 150 into the retraction barrel.

An alternative embodiment of the present invention is shown in FIGS. 12-22. FIGS. 12-22 show a retractable syringe assembly 200 that includes a fluid barrel 210 and a retraction barrel 220 as otherwise described herein. The retractable syringe also includes a needle hub assembly 240, a plunger rod 260, stopper 270 and a trigger element 290. The fluid barrel shown in FIGS. 14-15, includes a distal end 211, a open proximal end 219, a sidewall 212 extending from the distal end 211 and the proximal end 219 including an inside surface 214 defining a chamber 215. The inside surface 214 defines a cross-sectional width and may include a reuse prevention feature. The distal end 211 includes a distal wall 217 that encloses the distal end 211. In the embodiment shown, the sidewall 212 includes a first aperture 218 for permitting fluid communication between the fluid barrel and the retraction barrel. As will be discussed in greater detail below, the first aperture 218 also permits fluid communication between a needle cannula disposed within the retraction barrel 220 and the retraction barrel 220 and the fluid barrel 210.

Figure 14:
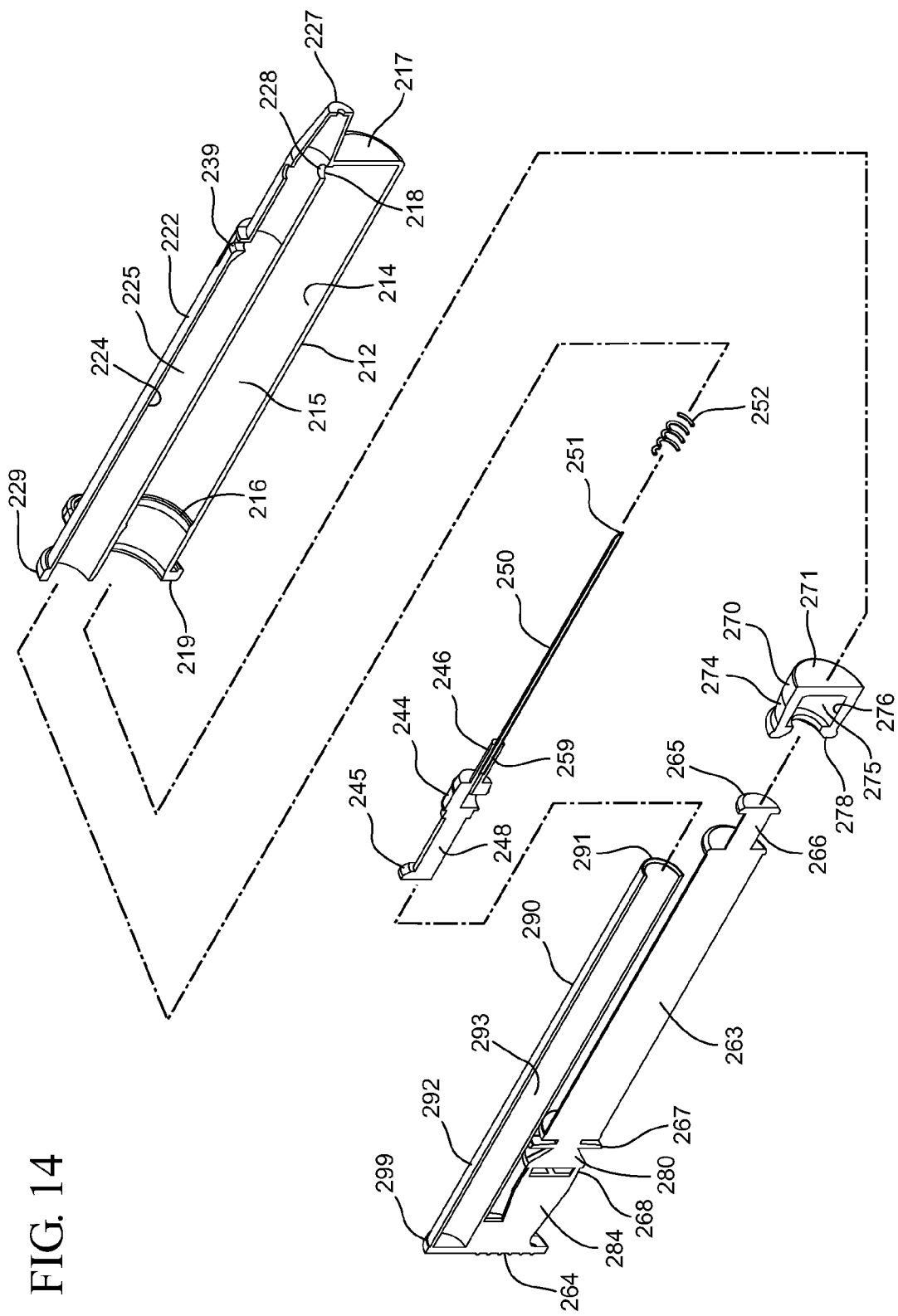
FIG. 14 illustrates a cross-sectional view of the syringe assembly of claim 13.
Figure 15:
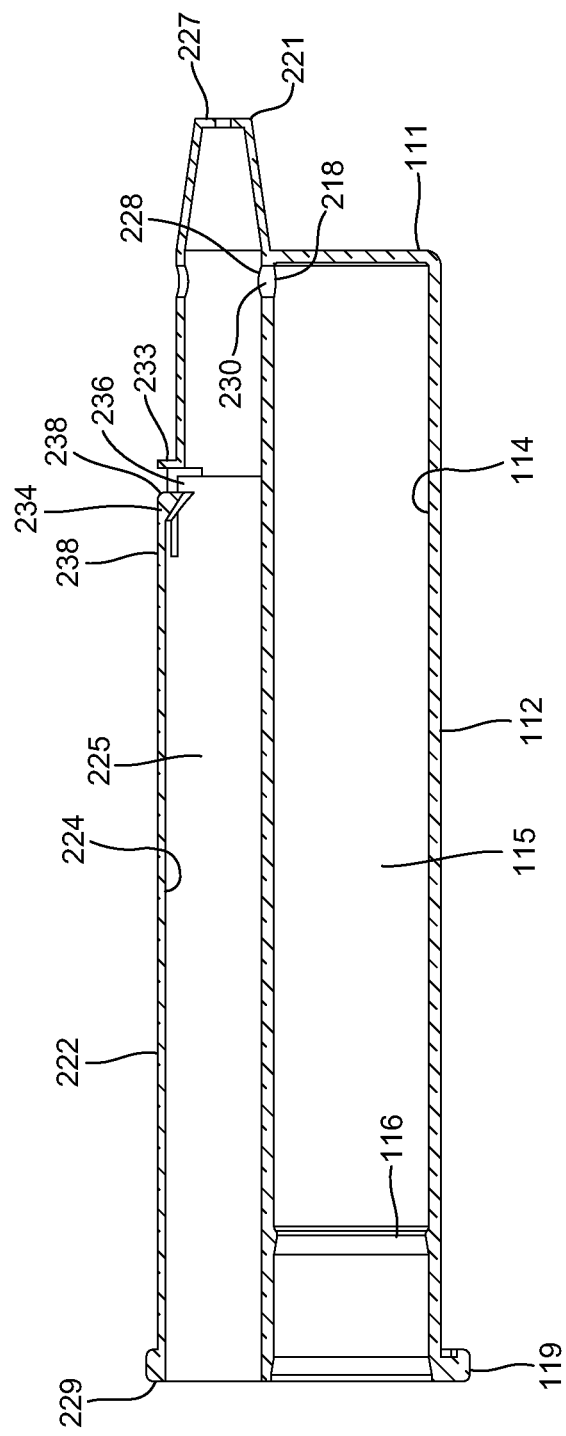
FIG. 15 illustrates a cross-sectional side-view of the fluid barrel and the retraction barrel shown in FIG. 12.
Figure 16:
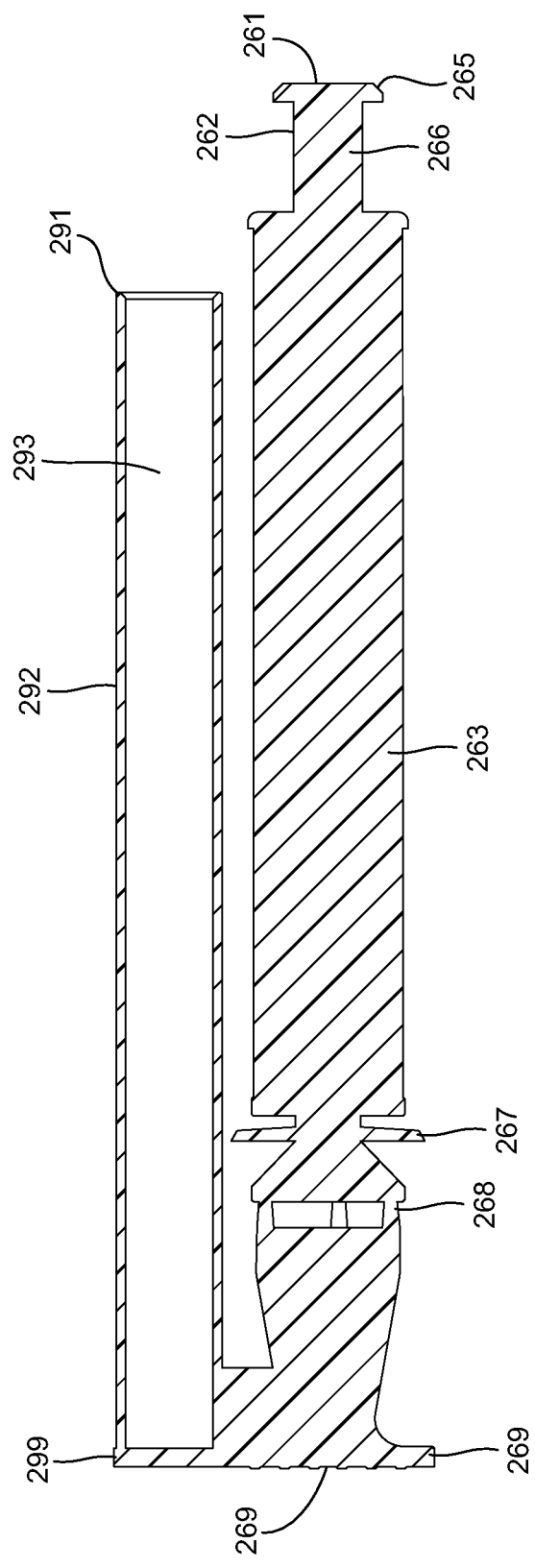
FIG. 16 illustrates a cross-sectional side-view of the plunger rod shown in FIG. 12.

The fluid barrel 210 shown in FIGS. 14-15 includes a reuse prevention feature. Specifically, the fluid barrel 210 includes a retaining element 216 shown in the form of a rib that extends around the entire circumference of the inside surface 214 of the fluid barrel 210 at a location adjacent to the proximal end 219 of the fluid barrel, as described above with reference to FIG. 4.

The retraction barrel 220 is disposed adjacent to the sidewall 212 of the fluid barrel 210 in the embodiment shown in FIGS. 14-15. The retraction barrel 220 is configured to house a needle hub assembly 240 therein and the retraction feature. The retraction barrel 220 includes an open distal end 221 and an open proximal end 229. A wall 222 having an interior surface 224 defining the needle chamber 225 extends from the open distal end 221 to the open proximal end 229. The wall 222 of the retraction chamber is adjacent to the sidewall 212 of the fluid barrel 210. In one or more embodiments, the wall 222 may extend around the portions of the retraction barrel 220 that are not in direct contact with fluid barrel 210 and the sidewall 212 may form the barrier between the retraction barrel 220 and the fluid barrel 210. In other words, the outside surface of the sidewall 212 may form the interior surface 224 of the retraction barrel 220 along the portion of the retraction barrel 220 that is in direct contact with the fluid barrel 210.

The size of the needle chamber 225 may be modified to accommodate the needle hub assembly 240 and/or the retraction feature. According to one or more embodiments, the interior surface 224 of the retraction barrel 220 has a cross-sectional width that is smaller than the first cross-sectional width of the fluid barrel 210. In specific embodiments, the cross-sectional width of the interior surface 224 of the retraction barrel is less than about 90%, 80%, 70%, 60%, 50%, 40%, 30%, or 20% of the cross-sectional width of the inside surface 214 of the fluid barrel. Such designs in which the cross-sectional width of the interior surface 224 of the retraction barrel is less than the cross-sectional width of the inside surface 214 of the fluid barrel, provides ergonomic and functional advantages. For example, the overall appearance and handling of the dual barrel syringe is more appealing to the user.

The open distal end 221 of the retraction barrel 220 in the embodiment shown includes a barrier wall 227 that partially encloses the open distal end 221. The open distal end 221 may be free of a barrier wall 227 and may be fully open. The wall 222 may include a second aperture 228 that permits fluid communication with the fluid chamber 215 and the needle chamber 225. The second aperture 228 of the wall may also allow fluid communication between the fluid chamber 215, needle chamber 225 and the needle cannula. The fluid communication between the fluid barrel 210 and retraction barrel 220 may be provided by a first conduit 230 that extends from a first aperture 218 of the fluid barrel 210 and the second aperture 228 of the retraction barrel. In the embodiment shown, the first conduit 230 extends along the width of the sidewall 212 and the wall 222.

The needle hub assembly may include a second conduit 232 that extends from an open end of the needle cannula to second aperture 228 of the retraction barrel. The second conduit 230 may include an opening 233 that must be aligned with the second aperture 228 to permit fluid communication between the needle cannula and the fluid barrel.

Figure 17:
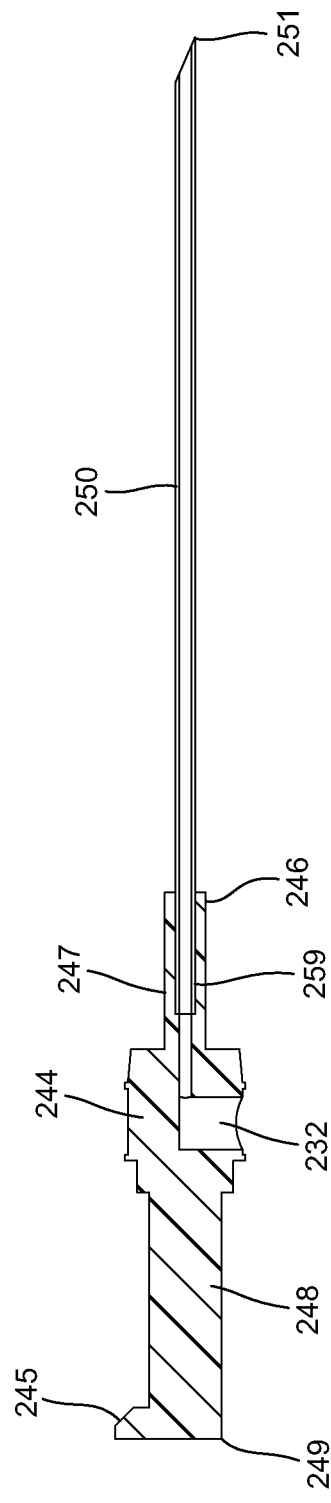
FIG. 17 illustrates a cross-sectional side-view of the needle hub assembly in FIG. 12.

The needle hub assembly 240 is disposed within the retraction barrel 220 and includes a needle hub 242 and a needle cannula 250 attached to the needle hub 242. The needle hub 242 includes a distal end 241 and a proximal end 249. The needle cannula 250 includes a free and open distal end 251 end and an open proximal end 259 that is attached to the distal end 241 of the needle hub. The needle hub 242 shown in FIG. 17 includes a needle hub body 244, a needle hub support 246 disposed distally adjacent to the needle hub body and a needle hub extension 248 that extends in the proximal direction from the needle hub body 244. The needle hub support 246 includes a recessed portion 247 for partially housing the proximal end 259 of the needle cannula. In the embodiment shown, the recessed portion 247 includes a portion of the second conduit 232 that extends through the needle hub 242 to the second aperture 228 of the retraction barrel. In one or more alternative embodiments, the proximal end 259 of the needle cannula may extend through the recessed portion 247 to the second conduit 232, which is located fully within the needle hub body 244 and does not extend into the needle cannula support 246. The needle hub extension 248 extends into the needle chamber 225 forms part of the retraction feature of the retractable syringe assembly 200. The needle hub extension 248 is shown in FIG. 17 is provided in the form of an elongate rod that is cylindrical in shape. However, the needle hub extension may have other shapes. The needle hub extension of the embodiments shown in FIG. 17 includes an outwardly extending latch portion 245 that engages the support element 234 of the wall, as will be described in greater detail below.

The needle cannula 250 of the needle hub assembly 240 is biased to move in the proximal direction. In the embodiment shown, the needle hub assembly 240 is biased to move in the proximal direction. In the embodiment shown, the needle hub assembly 240 is biased to move in the proximal direction by a biasing element 252 disposed between the needle hub 242 and the barrier wall 227 of the retraction barrel 220. The biasing element 252 may include a spring 253, which may be a compression spring that applies a constant force on the needle hub 242 in the proximal direction. In alternative embodiments, the biasing element 252 may be provided in another form, for example, a lever arm (not shown) may be disposed between the needle hub and the barrier wall. The retraction barrel 220 includes a supporting element 234 that prevents the needle hub from moving in the proximal direction. As will be explained in greater detail below, the release of the supporting element 234 will allow the biased needle hub 242 and the needle cannula 250 attached thereto to retract into the retraction barrel 220. In one or more variants, portion of the needle hub 242 may be biased. For example, the needle cannula support 246 and the needle hub extension 248 may be provided as separate components from the needle hub body 244 and may be biased and so that when the support element 234 is released, the needle hub extension 248 and the needle cannula support 246 may be retracted with the needle cannula 250 into the retraction barrel 220, while the needle hub body 244 remains stationary.

The needle hub assembly is sized moveable within the needle chamber. The size and shape of the needle hub assembly may be modified to permit movement in needle chambers having different sizes. In the assembled state, prior to use, the needle hub assembly is positioned at the open distal end of the retraction barrel.

The wall 222 of the retraction barrel 220 includes the supporting element 234 that engages at least a portion of the needle hub assembly 240 or interacts with the needle hub assembly 240 to provide a force in the distal direction to the needle hub assembly 240 such that the needle hub assembly 240 is positioned at the open distal end 221 of the retraction barrel. Specifically, the needle hub assembly 240 is positioned so the needle cannula 250 extends beyond the open distal end 221 of the retraction barrel in a first position. In the first position, the supporting element 234 engages the latch portion 245 of the needle hub extension 248 and allies a force on the needle hub 242 in the distal direction that is greater than the force applied to the needle hub 242 in the proximal direction by the biasing element 252. The supporting element 234 in the embodiment shown is provided in the form of a flexible arm 235 that is attached to the wall 222 of the retraction barrel. The wall 222 includes an opening 236 that permits the flexible arm 235 to flex outwardly. In the embodiment shown, the flexible arm 235 includes a distal end 237 that is attached to the wall 222 and a free proximal end 238 including a tab 239 that extends radially inwardly into the needle chamber 225. The tab 239 specifically engages the latch portion 245 of the needle hub extension and supports the needle hub extension 248. The tab 239 and the flexible arm 235 are sized and shaped to engage the latch portion 245 of the needle hub extension and to compress the biasing element 252 so the needle hub assembly is positioned in the first position. To retract the needle cannula 250 into the retraction barrel 220, as will be described in greater detail below, the flexible arm 235 is moved to release the latch portion 245 of the needle hub assembly 240. In other words, the flexible arm 235 is moved to a position in which the tab 239 is not longer engaged with the latch portion 245 and the support element 234 no longer applies a force on the needle hub extension 248 or needle hub 242 in the distal direction that is greater than force applied to the needle hub 242 in the proximal direction by the biasing element 252.

A plunger rod 260 is disposed within the fluid chamber 225. The plunger rod 260 includes a distal end 261 and a proximal end 269. The plunger rod 260 includes a stopper-engaging portion 262 extending from the distal end 261 to a plunger rod body 263. In one or more embodiments, the plunger rod body 263 may extend from the stopper-engaging portion 262 to the proximal end 269 of the plunger rod. In the embodiment shown in FIG. 16, the plunger rod body 263 extends from the stopper-engaging portion 262 to a reuse prevention feature that extends from the plunger rod body 263 to a thumb press 264 that is disposed at the proximal end 269 of the plunger rod. The thumb press 264 may include a thumb press support 284.

The stopper-engaging portion 262 includes an annular disc 265 disposed at the distal end of the plunger rod and a narrowed portion 266 extending from the annular disc 265 to the plunger rod body 263. The annular disc 265 engages a stopper 270 so it is disposed at the distal end of the plunge rod. In one or more embodiments, the narrowed portion 266 of the plunger rod 260 and the stopper 270 may be shaped to provide relative movement of the plunger rod 260 with respect to the stopper 270. In one or more alternative embodiments, the plunger rod 260 may be attached to the stopper 270 in a fixed relationship.

As shown in FIG. 14, the stopper 270 has a distal end 271, a proximal end 279, a stopper body 272 and a peripheral edge 273 which forms a seal with the inside surface 214 of the fluid barrel 210. In one or more embodiments, the peripheral edge 283 of the stopper 270 has cross-sectional width that permits the stopper 270 to slide in the proximal and distal directions within the fluid barrel. The stopper 270 may include an optional elongate tip (not shown) on its distal end 271 to facilitate reduction of the residual fluid and expulsion of fluid from the fluid barrel.

The stopper 270 includes a stopper body 274 extending from the peripheral edge 273 to the proximal end 279. The stopper body 274 includes a recess 275 that is defined by an inside surface 276. The recess 275 includes a neck portion 277 disposed adjacent to the proximal end 279, wherein the cross-sectional width of the inside surface 276 at the neck portion 277 is less than the cross-sectional width of the inside surface 276 at the remaining locations of the recess 275. The recess 275 allows the stopper-engaging portion 262 of the plunger rod 260 to connect to the stopper 270. The annular disc 265 engages the neck portion 277 to retain the stopper 270 on the plunger rod 260. In one or more alternative embodiments, detents (not shown) or tabs (not shown) on the stopper 270 and/or the stopper-engaging portion 262 may be used to retain the stopper 270 on the plunger rod 260.

Figure 18:
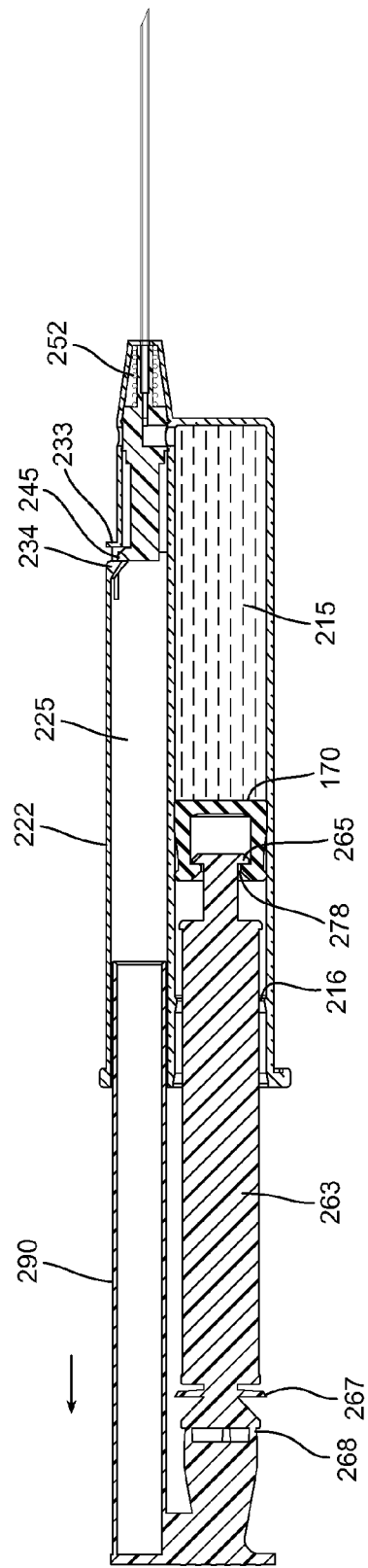
FIG. 18 illustrates a cross-sectional view of the syringe assembly of FIG. 12 after a force in the proximal direction has been applied to the plunger rod to fill the fluid chamber with liquid.
Figure 19:
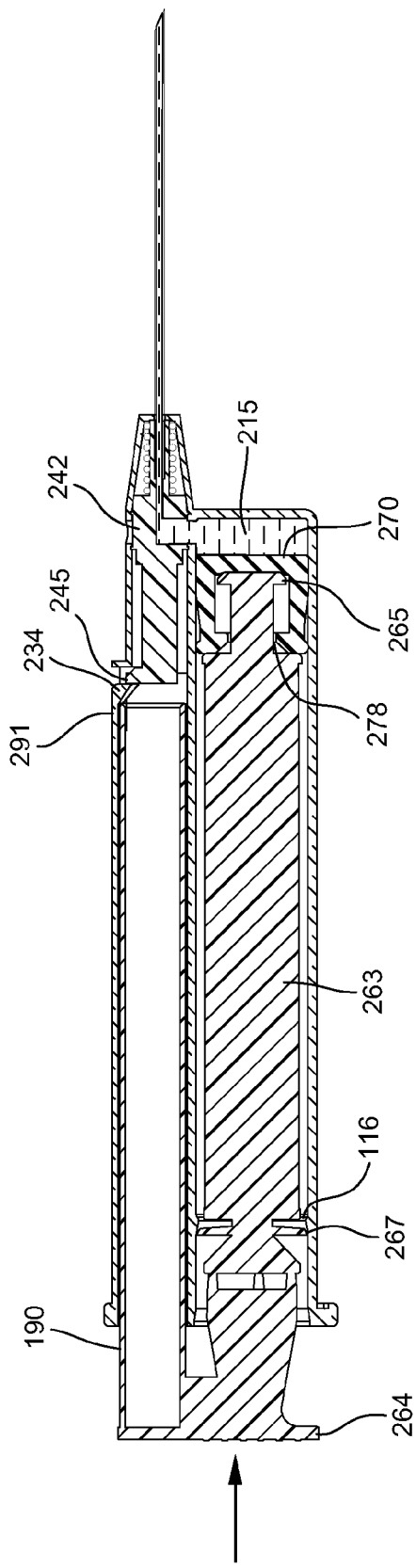
FIG. 19 illustrates a cross-sectional view of the syringe assembly of FIG. 18 after a force in the distal direction has been applied to the plunger rod to expel the liquid from the fluid chamber.

The plunger rod 260 and the stopper 270 have structure to provide relative movement of the plunger rod 26 with respect to the stopper 270, as described above with reference to FIGS. 5 and 7-8. FIGS. 18-19 illustrate structure to provide relative movement of the plunger rod 260 and the stopper 270. Specifically, the stopper-engaging portion 262 is able to move in the proximal and distal directions within the recess 265 of the stopper. When the stopper-engaging portion 262 is positioned adjacent to or in contact with the neck portion 278, the length of the plunger rod and stopper is maximized. When the stopper-engaging portion 262 is disposed at a distance from the neck portion 278 the length of the plunger rod and the stopper is shortened.

The plunger rod 260 may also include a reuse prevention feature, for example, a flexible protrusion 267 as described above with reference to FIGS. 5 and 7-11 that interacts with a retaining element 226 disposed on the inside surface 224 of the fluid barrel, as described above with reference to FIGS. 4 and 7-11. The plunger rod 260 may also include a frangible portion 268 that breaks upon application of a force on the plunger rod 260 in the proximal direction after the reuse prevention feature is activated and the plunger rod 260 is locked within the fluid barrel 210.

Figure 20:
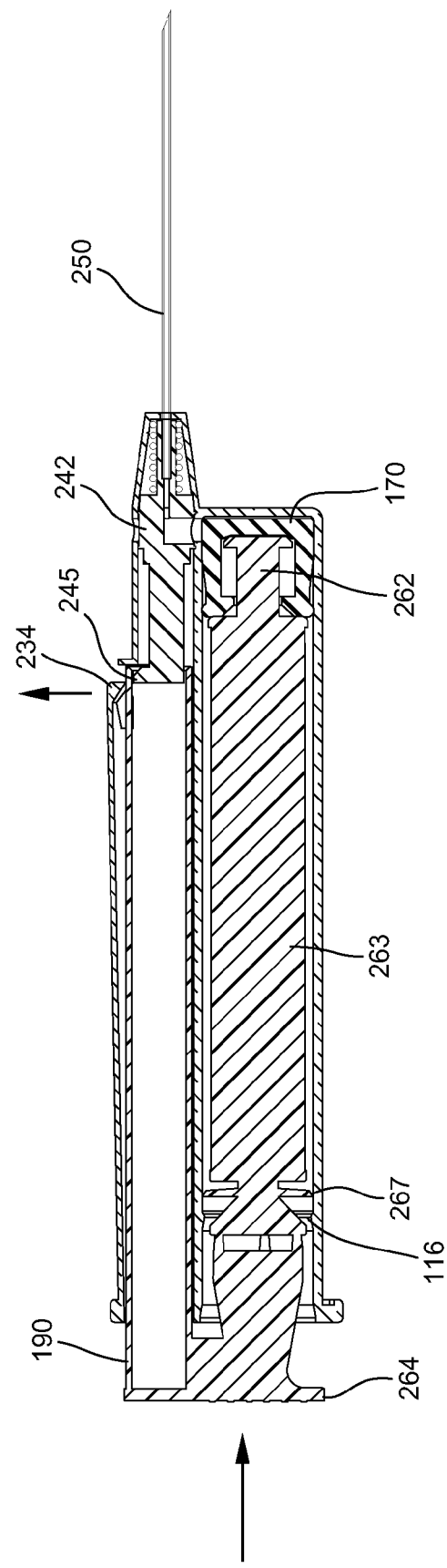
FIG. 20 illustrates a cross-sectional view of the syringe assembly of FIG. 19 after all of the liquid has been expelled from the fluid chamber and the stopper is in contact with the distal wall.
Figure 21:
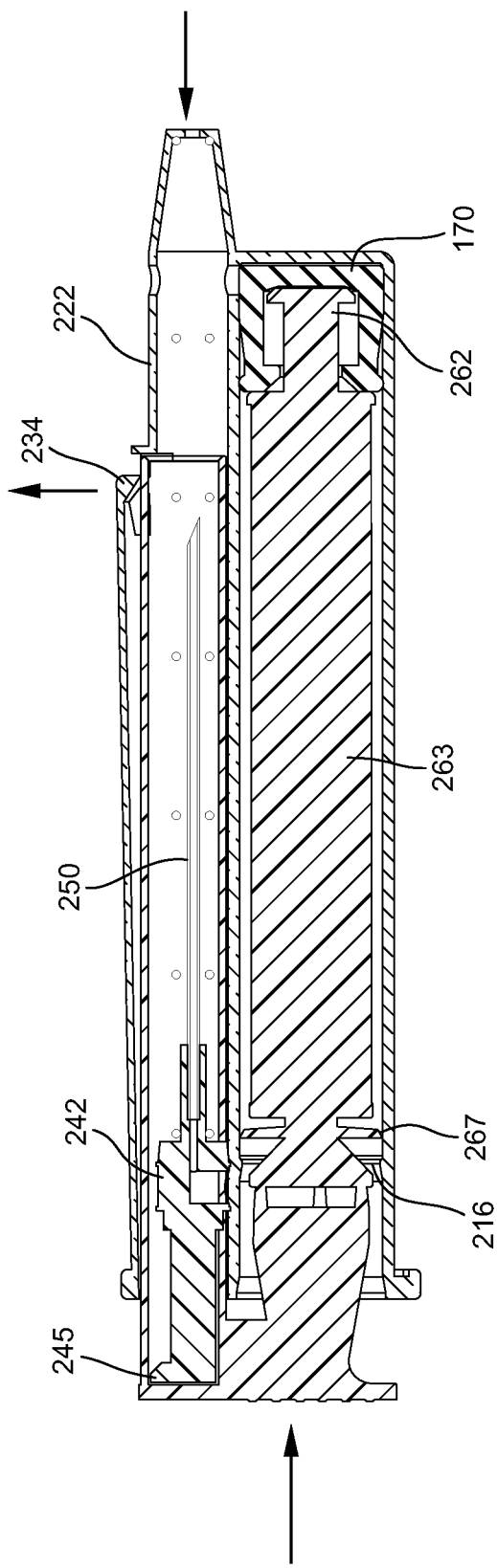
FIG. 21 illustrates a cross-sectional view of the syringe assembly of claim 20 after the needle hub assembly is retracted into the retraction barrel
Figure 22:
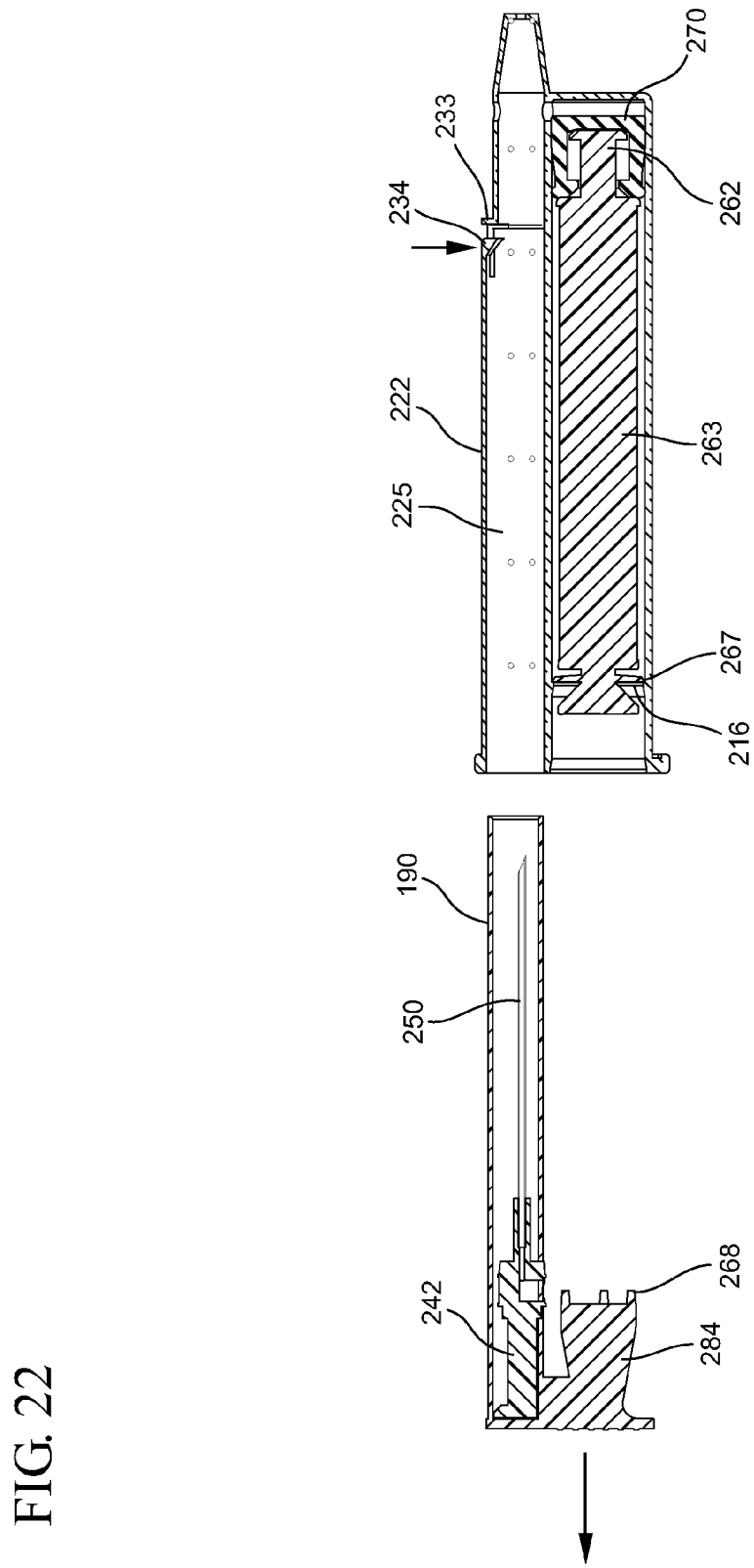
FIG. 22 illustrates a cross-sectional view of the syringe assembly of FIG. 21 after a force is applied on the plunger rod in the proximal direction, after the plunger rod is locked within the fluid barrel.

In use, as shown in FIG. 20, the stopper 270 is in contact with the distal wall 217 of the fluid barrel. In embodiments which utilize a plunger rod and stopper that permit relative movement of the plunger rod with respect to the stopper, the plunger rod is positioned such that the stopper-engaging portion 272 is in contact or adjacent to the neck portion 278. The length of the plunger rod 260 and the stopper 270 is maximized in this configuration. As the user applies a force on the plunger rod in the proximal direction to fill the fluid barrel, the plunger rod 260 and the stopper 270 move together in the proximal direction. The vacuum created by this movement draws liquid into the fluid barrel 210. In embodiments which utilize a reuse prevention feature on the plunger rod and/or fluid barrel, the reuse prevention feature is not yet activated. In embodiments which utilize a flexible protrusion on the plunger rod and a retaining element on the syringe barrel, as described above with respect to FIGS. 7-11, the flexible protrusion 267 remains positioned proximally adjacent to the retaining element 216.

After the desired amount of liquid is drawn into the fluid barrel 210, the user applies a force on the plunger rod 260 in the distal direction. In the embodiment shown, the trigger element 290 and the plunger rod 260 are attached as a single unit and therefore, the trigger element 290 moves with the plunger rod 260 in the distal direction.

When the entire contents of the fluid barrel 210 are expelled and the stopper 270 is in contact with the distal wall 217, the trigger element 290 applies a trigger force on the support element 234 and causes the support element 234 to move radially outwardly such that the tab 239 is no longer engaged with the latch portion 245 and the force applied to the needle hub 242 by the biasing element 152 causes the needle hub 242 and the needle cannula 250 to retract into the retraction barrel. When the stopper is in contact with the distal wall 217, the protrusion 267 moves distally past the retaining element 216 of the fluid barrel 210 and locks the plunger rod 260 into the fluid barrel 210. Application of a force in the proximal direction on the plunger rod 260 that is greater than the break force required to break the frangible portion 268 of the plunger rod 260.

A third aspect of the retractable syringe assembly 300 is shown in FIGS. 23-27. The retractable syringe assembly includes a single barrel 301 with a dividing wall 302 that divides the barrel 301 into a fluid barrel 310 and a retraction barrel 320.

In the embodiment shown in FIG. 23, the retractable syringe assembly includes a fluid barrel 110 and a retraction barrel 120. The retractable syringe also includes a needle hub assembly 140, a plunger rod 160, stopper 170 and a trigger element 190.

The fluid barrel 310 may include reuse prevention feature that cooperates with the reuse prevention feature on the plunger rod 360. As described in above with reference to FIGS. 7-11, the stopper 370 and the plunger rod 360 may have features that allow relative movement of the plunger rod 360 with respect to the stopper 370, as described above with respect to FIGS. 7-11. In one or more alternative embodiments, the plunger rod 360 may be attached to the stopper 370 in a fixed relationship.

The fluid barrel 310 and the retraction barrel 320 include a distal end 311, a open proximal end 319, a sidewall 312 extending from the distal end 311 and the proximal end 319 including an inside surface 314 defining a chamber 315. The inside surface 314 defines a cross-sectional width and may include a reuse prevention feature, that will be discussed in greater detail below. The distal end 311 of the fluid barrel 310 includes a distal wall 317 that encloses the distal end 311, while the distal end 311 of the retraction barrel includes an opening 322. In the embodiment shown, the dividing wall 302 includes a first aperture 318 for permitting fluid communication between the fluid barrel and the retraction barrel. As will be discussed in greater detail below, the first aperture 318 also permits fluid communication between a needle cannula disposed within the retraction barrel 320 and the retraction barrel 320 and the fluid barrel 310.

The retraction barrel 320 is configured to house a needle hub assembly 340 therein and the retraction feature. The retraction barrel 320 includes an open distal end 321 and a closed proximal end 329. The sidewall 312 and the dividing wall 302 form a needle chamber 325 that extends from the open distal end 321 to the open proximal end 329. The size of the needle chamber 325 may be modified to accommodate the needle hub assembly 340 and/or the retraction feature. According to one or more embodiments, the interior surface 324 of the retraction barrel 320 has a cross-sectional width that is smaller than the first cross-sectional width of the fluid barrel 310. In specific embodiments, the cross-sectional width of the interior surface 324 of the retraction barrel is less than about 90%, 80%, 70%, 60%, 50%, 40%, 30%, or 20% of the cross-sectional width of the inside surface 314 of the fluid barrel. Such designs in which the cross-sectional width of the interior surface 324 of the retraction barrel is less than the cross-sectional width of the inside surface 314 of the fluid barrel, provides ergonomic and functional advantages. For example, the overall appearance and handling of the dual barrel syringe is more appealing to the user.

The open distal end 321 of the retraction barrel 320 in the embodiment shown includes a tapered 327 that partially encloses the open distal end 321. In an alternative embodiment, the open distal end 321 may be free of a barrier wall 327 and may be fully open. The first aperture 318 of the wall may also allow fluid communication between the fluid chamber 315, needle chamber 325 and the needle cannula. The fluid communication between the fluid barrel 310 and retraction barrel 320 may be provided by a first conduit 330 that extends from a first aperture 318 of the fluid barrel 310.

The needle hub assembly may include a second conduit 332 that extends from an open end of the needle cannula to second aperture 328 of the retraction barrel. The second conduit 330 may include an opening 333 that must be aligned with the second aperture 328 to permit fluid communication between the needle cannula and the fluid barrel.

The needle hub assembly 340 is disposed within the retraction barrel 320 and includes a needle hub 342 and a needle cannula 350 attached to the needle hub 342. The needle hub 342 includes a distal end 341 and a proximal end 349. The needle cannula 350 includes a free and open distal end 351 end and an open proximal end 359 that is attached to the distal end 341 of the needle hub. The needle hub 342 shown in FIG. 23-27 may be the same as described above with reference to FIG. 17.

The needle cannula 350 of the needle hub assembly 340 is biased to move in the proximal direction. In the embodiment shown, the needle hub assembly 340 is biased to move in the proximal direction. In the embodiment shown, the needle hub assembly 340 is biased to move in the proximal direction by a biasing element 352 disposed between the needle hub 342 and the barrier wall 327 of the retraction barrel 320. The biasing element 352 as otherwise described herein that applies a constant force on the needle hub 342 in the proximal direction. In alternative embodiments, the biasing element 352 may be provided in another form, for example, a lever arm (not shown) may be disposed between the needle hub and the barrier wall. The retraction barrel 320 includes a supporting element 334 that prevents the needle hub from moving in the proximal direction. As will be explained in greater detail below, the release of the supporting element 334 will allow the biased needle hub 342 and the needle cannula 350 attached thereto to retract into the retraction barrel 320. In one or more variants, portion of the needle hub 342 may be biased.

The needle hub assembly is sized moveable within the needle chamber. The size and shape of the needle hub assembly may be modified to permit movement in needle chambers having different sizes. In the assembled state, prior to use, the needle hub assembly is positioned at the open distal end of the retraction barrel.

In the embodiment shown in FIGS. 23-27, the retraction mechanism is not driven by a separate trigger element but rather, by the internal structure of the plunger rod 360 and the syringe barrel 301. Specifically, the dividing wall 302 includes a supporting element 303 that engages at least a portion of the needle hub assembly 340 or interacts with the needle hub assembly 340 to provide a force in the distal direction to the needle hub assembly 340 such that the needle hub assembly 340 is positioned at the open distal end 321 of the retraction barrel. Specifically, the needle hub assembly 340 is positioned so the needle cannula 350 extends beyond the open distal end 321 of the retraction barrel in a first position. In the first position, the supporting element 334 provides a force on the needle hub 342 in the distal direction that is greater than the force applied to the needle hub 342 in the proximal direction by the biasing element 352. The supporting element 334 in the embodiment shown is provided in the form of a perpendicular tab 304 that is disposed on the dividing wall 302 and extends into the needle chamber 325 and a ramped portion 307 that is disposed on the dividing wall 302 and extends into the fluid chamber 315. The dividing wall 302 includes an opening 305 that permits the perpendicular tab 304 to flex outwardly into the fluid chamber 325 as the plunger rod interacts with the ramped portion 307. In the embodiment shown, the portion of the dividing wall 302 adjacent to the perpendicular tab 304 also flexes inwardly to move the perpendicular tab 304. The perpendicular tab 304 is sized and shaped to support the needle hub 342 and the needle cannula 350 and to compress the biasing element 352 so the needle hub assembly is positioned in the first position. To retract the needle cannula 350 into the retraction barrel 320, as will be described in greater detail below, the perpendicular tab 304 is moved to release the needle hub assembly 340. In other words, the perpendicular tab 304 is moved to a position in which it can no longer support the needle hub 342 and apply a force on the needle hub 342 in the distal direction that is greater than force applied to the needle hub 342 in the proximal direction by the biasing element 352.

The retraction mechanisms utilized in the retractable syringe assemblies 100, 200 and 300 described herein may be substituted with the retraction mechanisms described in provisional application P-9275. Specifically, the retraction mechanisms shown in FIGS. 8-12, 24-29 and 33-37.

A plunger rod 360 is disposed within the fluid chamber 325. The plunger rod 360 includes a distal end 361 and a proximal end 369. The plunger rod 360 includes a stopper-engaging portion 362 extending from the distal end 361 to a plunger rod body 363, which may be shaped and sized as described otherwise herein with respect to retractable syringe assemblies 100 and 200. In one or more embodiments, the plunger rod body 363 may extend from the stopper-engaging portion 362 to the proximal end 369 of the plunger rod. In the embodiment shown in FIGS. 23-27, the plunger rod body 363 extends from the stopper-engaging portion 362 to a reuse prevention feature that extends from the plunger rod body 363 to a thumb press 364 that is disposed at the proximal end 369 of the plunger rod. The thumb press 364 may include a thumb press support 384.

The plunger rod body 363 includes a projection 306 that extends radially outwardly from the plunger rod body 363. The projection 306 is shaped, sized and positioned to interact with the ramped portion 307 of the dividing wall 302. Specifically, the projection 306 applies a distally directed force on the ramped portion 307 to cause the dividing wall 302 and the perpendicular tab 304 to flex or move into the fluid chamber, thereby releasing the force applied to the needle hub 342 in the distal direction and allowing the force applied to the needle hub 342 by the biased element 352 to retract the needle hub and needle cannula into the retraction barrel. The stopper 370 is attached to the stopper engaging portion 362 and may be shaped and sized as described otherwise with reference to retractable syringe assemblies 100 and 200. The stopper 370 may be shaped and sized and include features to permit the plunger rod to move in the proximal and distal directions relative to the stopper.

Figure 24:
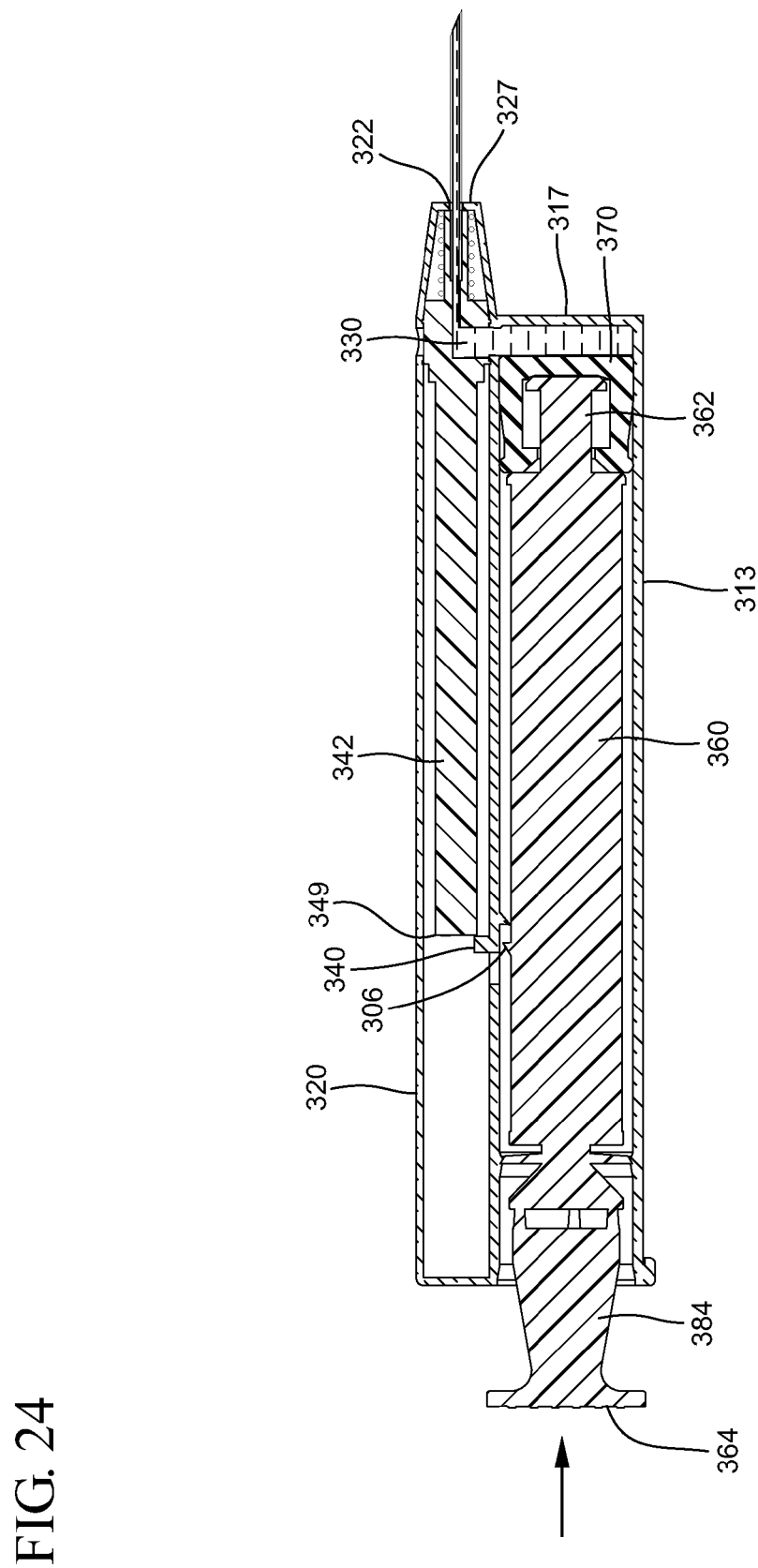
FIG. 24 illustrates a cross-sectional side view of the retractable syringe assembly shown in FIG. 23 after a force is applied to the plunger rod in the distal direction.
Figure 26:
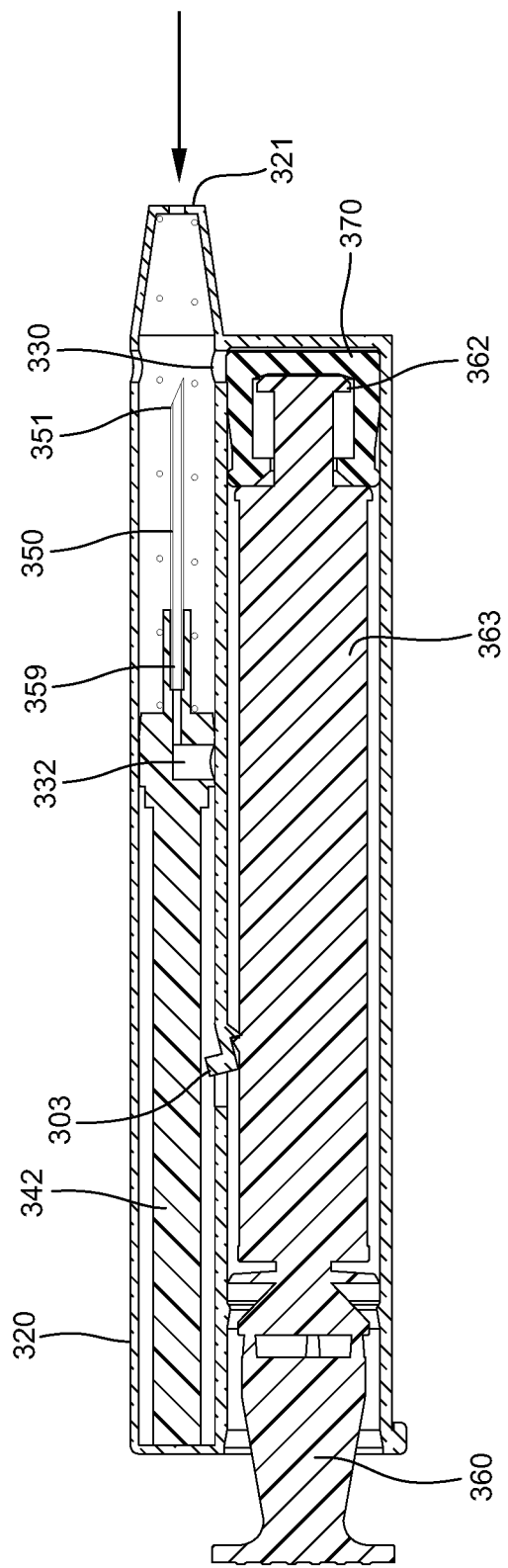
FIG. 26 illustrate cross-sectional view of the syringe assembly of claim 25 after the needle hub assembly is retracted into the retraction barrel.
Figure 27:
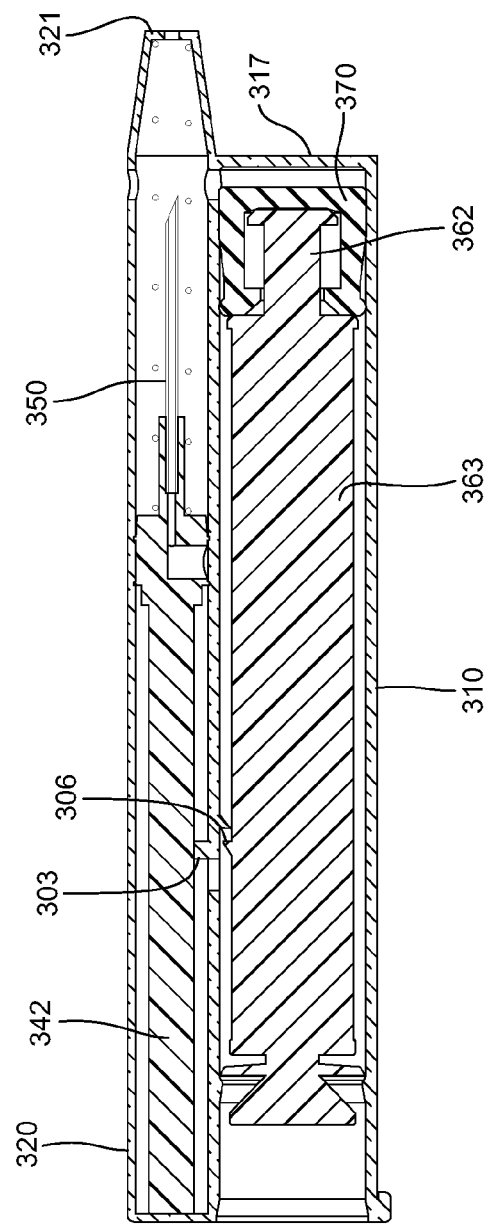
FIG. 27 illustrates a cross-sectional view of the syringe assembly of FIG. 26 after a force is applied on the plunger rod in the proximal direction, after the plunger rod is locked within the fluid barrel.
Figure 27:
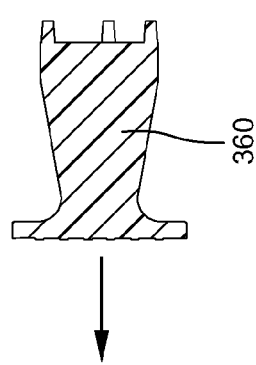

As shown in FIGS. 24-25, after the desired amount of fluid is aspirated into the fluid barrel, a force is applied to the plunger rod 360 in the distal direction to expel the contents of the fluid barrel. As the plunger rod 360 moves in the proximal direction and the projection 306 applies a force on the ramped portion 307 in the distal direction that causes the dividing wall 302 and the perpendicular tab 304 to flex inwardly and release the needle hub so that the biasing element causes the needle hub to retract into the retraction barrel, as shown in FIG. 26. The reuse prevention features of the retractable syringe barrel also lock the plunger rod 360 into the fluid barrel 310 as otherwise described herein and as shown in FIG. 27.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
a fluid barrel including a sidewall having an inside surface defining a fluid chamber for retaining fluid and having a first cross-sectional width, an open proximal end and a distal end including a distal wall;
a plunger rod disposed within the fluid chamber comprising a distal end, a proximal end, a plunger rod body extending from the distal end to the proximal end, and a stopper disposed at the distal end of the plunger rod for forming a fluid-tight seal with the inside surface of the barrel;
a retraction barrel disposed adjacent to the sidewall of the fluid barrel, the retraction barrel including a wall having an interior surface defining a needle chamber, an open proximal end, an open distal end including a barrier wall, an aperture between the wall of the retraction barrel and the sidewall of the fluid barrel such that the fluid chamber and the needle chamber are in fluid communication and a needle hub assembly comprising a needle hub, a needle cannula attached to the needle hub in fluid communication with the aperture, the needle hub assembly biased to move in the proximal direction; and
a trigger element moveable with the plunger rod and extending into the needle chamber of the retraction barrel, the trigger element providing a trigger force causing the needle cannula to retract into the retraction barrel.

2. The syringe assembly of claim 1, wherein the wall includes a supporting element that engages a needle assembly disposed within the needle chamber and the supporting element is positioned to apply a force in the distal direction to the needle hub such that the needle cannula extends distally beyond the open distal end of the retraction barrel in a first position.

3. The syringe assembly of claim 2, wherein the trigger element provides a trigger force on the needle hub to disengage the supporting element and the needle hub so the needle cannula is housed within the retraction barrel.

4. The syringe assembly of claim 1, wherein the needle hub is biased by a spring disposed between the needle hub and the barrier wall that exerts a force on the needle hub in the proximal direction.

5. The syringe assembly of claim 1, wherein the trigger element is attached to the proximal end of the plunger rod.

6. The syringe assembly of claim 5, wherein the trigger element includes a proximal end attached to the proximal end of the plunger rod, a free and open distal end that provides the trigger force, and a trigger element body extending from the proximal end to the distal end and including an interior surface defining a hollow interior.

7. The syringe assembly of claim 6, wherein the open distal end of the trigger element comprises a beveled edge that extends distally.

8. The syringe assembly of claim 1, wherein the inside surface of the fluid barrel includes a retaining ring adjacent said proximal end defining a second cross-sectional width that is less than the first cross-sectional width and the plunger rod body includes a flexible protrusion having a cross-sectional width greater than the cross-sectional width of the fluid barrel at the retaining ring.

9. The syringe assembly of claim 1, wherein the plunger rod body comprises a distal portion and a proximal portion, the protrusion disposed between the distal portion and the proximal portion.

10. The syringe assembly of claim 9, wherein the distal portion of the plunger rod body comprises a support member disposed proximally adjacent to the flexible protrusion and at least one frangible portion disposed proximally adjacent to the support member.

11. The syringe assembly of claim 10, wherein the distal end of the plunger rod includes a stopper-engaging portion and the stopper is attached to the stopper-engaging portion of the plunger rod, the stopper being distally and proximally movable relative to the stopper-engaging portion for a preselected axial distance such that when the distal end of the stopper is in contact with the distal wall of the barrel, the protrusion is permitted to advance distally past the rib in the barrel and lock the plunger rod in the barrel to prevent reuse of the syringe assembly.

12. The syringe assembly of claim 11, wherein the stopper-engaging portion of the plunger rod is connected to the stopper such that upon application of an initial proximally directed force to the plunger rod, while holding the barrel, causes the plunger rod and the trigger element to move the length of the axial distance in a proximal direction within the barrel, while the stopper remains stationary.

13. The syringe assembly of claim 12, wherein the stopper-engaging portion of the plunger rod is connected to the stopper such that upon application of a continuous proximally directed force to the plunger rod, while holding the barrel, causes the stopper, the plunger rod and the trigger element to move together in a proximal direction within the barrel.

14. The syringe assembly of claim 13, wherein the stopper-engaging portion of the plunger rod is connected to the stopper such that application of an initial distally directed force to the plunger rod after application of a proximally directed force to the plunger rod, while holding the barrel, causes the stopper to remain stationary and the plunger rod and the trigger element to move the length of the axial distance in the distal direction within the barrel.

15. The syringe assembly of claim 14, wherein the stopper-engaging portion of the plunger rod is connected to the stopper such that application of a continuous distally directed force to the plunger rod causes the stopper, plunger rod and the trigger element to move together in the distal direction within the barrel until the stopper reaches the distal end of the barrel.

16. The syringe barrel of claim 15, wherein contact between the stopper and the distal wall of the barrel causes the support element to disengage from the needle hub and the protrusion to advance distally past the rib in the barrel and lock the plunger rod in the barrel to prevent reuse of the syringe assembly.

17. The syringe assembly of claim 16, wherein application of a proximally directed force to the plunger, after the protrusion has advanced distally past the rib, causes the at least one frangible portion of the plunger rod to break.

18. The syringe assembly of claim 11, wherein application of a continuous proximally directed force on the plunger rod causes the stopper-engaging portion to disengage from the stopper.

19. The syringe assembly of claim 9, wherein the proximal end of the trigger element is attached to a thumb press of the plunger rod.

20. The syringe assembly of claim 1, wherein the retraction barrel is disposed parallel to the fluid barrel.

21. The syringe assembly of claim 1,
wherein the retraction barrel is nested with the fluid barrel and the retraction barrel has cross-sectional dimension that is less than 90% of the cross-sectional dimension of the fluid barrel.

22. A syringe assembly comprising: a barrel comprising including an open proximal end, sidewall having an inside surface defining a fluid chamber for retaining fluid and having a first cross-sectional width and a needle chamber for housing a needle hub assembly, the fluid chamber and the needle chamber being divided by a barrier wall having a first aperture permitting fluid communication between the fluid chamber and the needle chamber, the needle chamber including a flexible tab that extends into the needle chamber to engage a needle hub assembly disposed therein; a needle hub assembly disposed within the needle chamber, the needle hub assembly comprising a needle hub, a needle cannula attached to the needle hub in fluid communication with the first aperture, the needle cannula biased to move in the proximal direction, the flexible tab positioned to engage the needle hub and apply a force in the distal direction to the needle hub so that the needle cannula extends beyond the open distal end of the retraction barrel in a first position; and a plunger rod disposed within the fluid chamber comprising a distal end, a proximal end, a stopper disposed at the distal end of the plunger rod for forming a fluid-tight seal with the inside surface of the barrel, a plunger rod body extending from the distal end to the proximal end, and an activation element disposed on the plunger rod to move the flexible tab and cause the needle cannula to retract and be housed within the retraction barrel in a second position.

23. The syringe assembly of claim 22, wherein the needle cannula is biased to move in the proximal direction by a spring disposed between the needle hub and the barrier wall that exerts a force on the needle hub and the spring is compressed when the flexible tab engages the needle hub.

24. The syringe assembly of claim 23, wherein the needle chamber barrier wall further comprises a second aperture to permit the flexible tab to flex inwardly into the needle chamber and a ramped portion that extends outwardly into the fluid chamber.

25. The syringe assembly of claim 24, wherein the disengagement of the flexible tab and the needle hub permits the spring to expand and causes the needle hub to retract into the hollow interior of the trigger element.

26. The syringe assembly of claim 25, wherein, upon application of a force in the proximal direction on the plunger rod causes the plunger rod to move in the proximal direction and aspirate a liquid into the fluid chamber and the sequential application of a force in the distal direction causes the plunger rod to engage the ramp and cause the flexible tab to flex outwardly into the fluid chamber to release the force applied to the needle hub in the distal direction.

27. The syringe assembly of claim 24, wherein the trigger element is disposed on the plunger rod body and extends radially outwardly from the plunger rod body.

28. The syringe assembly of claim 22, wherein the barrel comprises a dose limit indicator disposed on an outside surface of the sidewall.

29. The syringe assembly of claim 22, wherein the inside surface of the side wall at the fluid chamber includes a retaining ring adjacent said proximal end defining a second cross-sectional width that is less than the first cross-sectional width and the plunger rod body includes a flexible protrusion having a cross-sectional width greater than the cross-sectional width of the fluid barrel at the retaining ring.

30. The syringe assembly of claim 29, wherein the contact between the stopper and the distal wall of the barrel causes the flexible tab to disengage from the needle hub and the protrusion to advance distally past the rib in the barrel and lock the plunger rod in the barrel to prevent reuse of the syringe assembly.

31. The syringe assembly of claim 29, wherein the distal end of the plunger rod includes a stopper-engaging portion and the stopper is attached to the stopper-engaging portion of the plunger rod, the stopper being distally and proximally movable relative to the stopper-engaging portion for a preselected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly.

32. The syringe assembly of claim 22, wherein the retraction barrel is nested with the fluid barrel and the retraction barrel has cross-sectional dimension that is less than 90% of the cross-sectional dimension of the fluid chamber.

* * * * *